United States Patent
Khan et al.

(10) Patent No.: US 9,797,913 B2
(45) Date of Patent: Oct. 24, 2017

(54) ALZHEIMER'S DISEASE-SPECIFIC ALTERATIONS OF THE ERK1/ERK2 PHOSPHORYLATION RATIO-ALZHEIMER'S DISEASE-SPECIFIC MOLECULAR BIOMARKERS (ADSMB)

(71) Applicant: BLANCHETTE ROCKEFELLER NEUROSCIENCES INSTITUTE, Morgantown, WV (US)

(72) Inventors: Tapan Kumar Khan, Gaithersburg, MD (US); Daniel L. Alkon, Bethesda, MD (US)

(73) Assignee: Blanchette Rockefeller Neuroscienses Inc., Morgantown, WV (US)

( * ) Notice: Subject to any disclaimer, the term of this patent is extended or adjusted under 35 U.S.C. 154(b) by 0 days.

(21) Appl. No.: 13/774,049

(22) Filed: Feb. 22, 2013

(65) Prior Publication Data
US 2014/0031245 A1    Jan. 30, 2014

Related U.S. Application Data

(63) Continuation of application No. 12/083,056, filed as application No. PCT/US2006/037186 on Sep. 25, 2006, now abandoned, which is a continuation-in-part of application No. PCT/US2006/022156, filed on Jun. 7, 2006, which is a continuation-in-part of application No. PCT/US2005/036014, filed on Oct. 11, 2005, which is a continuation-in-part of application No. 11/246,524, filed on Oct. 11, 2005, now Pat. No. 7,595,167.

(51) Int. Cl.
G01N 33/68    (2006.01)

(52) U.S. Cl.
CPC . G01N 33/6896 (2013.01); G01N 2333/4709 (2013.01); G01N 2333/912 (2013.01); G01N 2800/2821 (2013.01)

(58) Field of Classification Search
None
See application file for complete search history.

(56) References Cited

U.S. PATENT DOCUMENTS

| | | |
|---|---|---|
| 5,242,932 A | 9/1993 | Gandy et al. |
| 5,385,915 A | 1/1995 | Buxbaum et al. |
| 6,077,686 A | 6/2000 | Der et al. |
| 6,080,582 A | 6/2000 | Alkon et al. |
| 6,080,784 A | 6/2000 | Driedger et al. |
| 6,107,050 A | 8/2000 | Alkon et al. |
| 7,468,389 B2 | 12/2008 | Nishizaki et al. |
| 7,595,167 B2 | 9/2009 | Khan et al. |
| 2001/0051344 A1 | 12/2001 | Shalon et al. |
| 2003/0108956 A1 | 6/2003 | Alkon et al. |
| 2003/0153014 A1 | 8/2003 | Shen et al. |
| 2004/0014678 A1 | 1/2004 | Favit et al. |
| 2004/0086905 A1 | 5/2004 | Das et al. |
| 2005/0059092 A1 | 3/2005 | Zhao et al. |
| 2005/0075393 A1 | 4/2005 | Tomoyuki |
| 2007/0082366 A1 | 4/2007 | Khan et al. |
| 2009/0029873 A1 | 1/2009 | Khan et al. |

FOREIGN PATENT DOCUMENTS

| | | |
|---|---|---|
| EP | 0 735 370 | 10/1996 |
| JP | 06-279311 | 10/1994 |
| JP | 10-090263 | 4/1998 |
| WO | WO 93/11231 A | 6/1993 |
| WO | WO 00/20867 | 4/2000 |
| WO | WO 00/70099 | 11/2000 |
| WO | WO 01/69244 | 9/2001 |
| WO | WO 02/10768 | 2/2002 |

(Continued)

OTHER PUBLICATIONS

Dineley et al., J Neurosci, 21:4125-4133, 2001.*
Balin et al., "Normal replicative lifespan of Alzheimer skin fibroblasts", Neurobiol Aging, vol. 9, pp. 195-198 (1988).
Becton, Dickenson& Co., BD Gentest™ Primary Hepatocytes, 13 (2008).
Clark et al.,,, "Evidence that the Bradykinin-induced Activation of Phospholipase D and of the Mitogen-activated Protein Kinase Cascade Involve Different Protein Kinase C. Isoforms," J. Biol. Chem. 270:7097-7103, 1995.
Cornforth et al., "Automated Classification Reveals Morphological Factors Associated with Dementia," Applied Computing, 8:182-190 (2008).
Cuenda et al., "Use of Kinase Inhibitors to Dissect Signaling Pathways," Methods in Molecular Biology,vol. 99, Humana Press Inc., Totowa, NJ (2000).
Est Profile Hs.400740, available at www.ncbi.nlm.nih.gov/UniGene, printed on Aug. 3, 2012, pp. 1-3.

(Continued)

*Primary Examiner* — Kimberly A. Ballard
*Assistant Examiner* — Stacey Macfarlane
(74) *Attorney, Agent, or Firm* — Finnegan, Henderson, Farabow, Garrett & Dunner LLP

(57) ABSTRACT

The present invention relates to methods of diagnosing Alzheimer's Disease as well as to methods of confirming the presence or absence of Alzheimer's Disease in a subject. The present invention is also directed to methods of identifying a lead compound useful for the treatment of Alzheimer's Disease by contacting non-Alzheimers cells with an amyloid beta peptide, stimulating the cells with a protein kinase C activator, contacting the cells with a test compound, and determining the value of an Alzheimer's Disease-specific molecular biomarker. The present invention is also directed to methods of diagnosing Alzheimer's Disease in a subject by detecting alterations in the ratio of specific phosphorylated MAP kinase proteins in cells after stimulation with a protein kinase C activator. The Alzheimer's Disease-specific molecular biomarkers disclosed herein are useful for the diagnosis of Alzheimer's Disease, monitoring the progression of Alzheimer's Disease in a subject and in screening methods for the identification of compounds for treating or preventing Alzheimer's Disease. The invention is also directed to kits containing reagents for the detection and diagnosis of the presence or absence of Alzheimer's Disease using the Alzheimer's Disease-specific molecular biomarkers disclosed herein.

7 Claims, 6 Drawing Sheets

(56) References Cited

FOREIGN PATENT DOCUMENTS

| WO | WO 02/50013 | 6/2002 |
|---|---|---|
| WO | WO 02/067764 | 9/2002 |
| WO | WO 03/102016 | 12/2003 |
| WO | WO 2004/083241 | 9/2004 |
| WO | WO 2006/050475 | 5/2006 |
| WO | WO 2006/054979 | 5/2006 |
| WO | WO 2007/043998 | 4/2007 |
| WO | WO 2007/044094 | 4/2007 |
| WO | WO 2007/047029 | 4/2007 |
| WO | WO 2007/149985 | 12/2007 |
| WO | WO 2008/100449 | 8/2008 |
| WO | WO 2008/148115 A1 | 12/2008 |

OTHER PUBLICATIONS

Johnson et al., "IQGAP1 regulation and roles in cancer", Cellular Signalling, vol. 21, pp. 1471-1478 (2009).
Kleinman et al., "Use of extracellular matrix components for cell culture", Analytical Biochemistry, 166, pp. 1-13, (1987).
Kuzirian et al., "Bryostatin Enhancement of Memory in Hermissenda", Biol. Bull. 210:201-214 (Jun. 2006).
Laurent-Matha et al., "Catalytically inactive human cathepsin D triggers fibroblast invasive growth", Journal of Cell Biology, vol. 168, No. 3, pp. 489-499, Jan. 31, 2005.
Pasinetti GM., "Use of cDNA Microarray in the Search for Molecular Markers Involved in the Onset of Alzheimer's Disease Dementia", J Neurosci Res., 65(6):471-476, Aug. 31, 2001.
Shaw et al., "Biomakers of neurodegeneration for diagnosis and monitoring therapeutics", vol. 6, pp. 295-303 (2007).
Solerte et al., "Hemorheological Changes and Overproduction of Cytokines from Immune Cells in Mild to Moderate Dementia of the Alzheimer's Type: Adverse Effects on Cerebromicrovascular System," Neurobiology of Aging, 21( 2):271-287 (2000).
Urbanelli et al., "Cathepsin D expression is decreased in Alzheimer's disease fibroblasts", Neurobiology of Aging, vol. 29, pp. 12-22 (2008).
Weeraratna et al., "Alterations in immunological and neurological gene expression patterns in Alzheimer's disease tissues", vol. 313, pp. 450-461 (2007).
Zhu et al., "The role of mitogenactivated protein kinase pathways in Alzheimer's disease," Neurosignals, 11(5):270-281, Sep. 2002.
Alkon et al., Protein Synthesis Required for Long-Term Memory is Induced by PKC Activation on Days Before Associative Learning, Proc. Natl. Acad. Sci. USA,102:16432-16437 (2005).
Anderson et al., "Oxidative Signaling and Inflammatory Pathways in Alzheimer's Disease," Biochem. Soc. Symp., 67:141-149 (2001).
Baker et al., "System Manifestation of Alzheimer's Disease," Age, 11:60-65 (1988).
Barrow et al., "Functional Phenotype in Transgenic Mice Expressing Mutant Human Presenilin-1," Nuerogiology of Disease 7, 119-126 (2000).
Bassa BV, et al.,"Lysophosphatidylcholine Activates Mesangial Cell PKKC and MAP Kinase by PLCy-1and Tyrosine Kinase-Ras Pathways," Am J Physiol, 277:F328-2337 (1999).
Bernier et al., "Bradykinin-regulated Interactions of the Mitogen-activated Protein Kinase Pathway with the Endothelial Nitric-oxide Synthase," J. Biol. Chem., 275:30707-30715 (2000).
Berridge, "Inositol Triphosphate and Diacylglycerol as Second Messengers," Biochem J., 220:345-360 (1984).
Biernat et al., "Phosphorylation of Ser 262 Strongly Reduces Binding of Tau to Microtubules: Distinction beteen PHF-like Immunoreactivity and Microtubule Binding," Neuron, 11:153-163 (1993).
Blanchard et al., "Hyperphosphorylation of Human TAU by Brain Kinase PK40et beyond Phosphorylation 12 by cAMP-dependent PKA: Relation to Alzheimer's Disease." Biochem. Biophys. Res. Commun., 200(1):187-194 (1994).
Bockman et al., "Kinins and Kinin Receptors: Importance for the Activation of Leukocytes," Journal of Leukocyte Biology, 68 (Nov. 2000).

Bondy et al., "The PHA-Induced Calcium Signal in Lymphocytes is Altered After Blockade of K+-Channels in Alzheimer's Disease," J. Psychiat. Res., 30(3):217-227 (1996).
Brooks et al., "Gene Expression Profiles of Metabolic Enzyme Transcripts in Alzheimer's Disease," Brain Res, 1127(1):127-135 (2007).
Burke et al., "Update on Alzheimer's Disease: Promising advances in Detection and Treatment," Postgraduate Medicine, 106(5) (1999).
Buxbaum et al., "Evidence That Tumor Necrosis Factor a Converting Enzyme Is Involved in Regulated a-Secretase Cleavage of the Alzheimer Amyloid Protein Precursor," The Journal of Biological Chemistry, 273(43):27765-27767 (1998).
Caporaso et al., "Protein Phosphorylation Regulates Secretion of Alzheimer B/A4 Amyloid Precursor Protein," Proc. Natl. Acad. Sci. USA, 89:3055-3059 (Apr. 1992).
Chapman et al., "Genes, Models and Alzheimer's Disease," Trends in Genetics, 17(5) (May 2001).
Connolly, G.P., "Fibroblast Models of Neurological Disorders: Fluorescence Measurement Studies", Trends Pharmacol. Sci. 19, 171-177 (1998).
Cruzblanca et al., "Bradykinin Inhibits M Current via Phospholipase C and Ca2+ Release from IP3-sensitive Ca1 + Stores in Rat Sympathetic Neurons, " Proc. Natl. Acad. Sci. USA, 95:7151-7156 (Jun. 1998).
De Leon et al., "Biomarkers for the early diagnosis of Alzheimer's disease," Neurology, 5 (Mar. 2006).
Dunckley et al., Gene Expression Correlates of Neurofibrillary Tangles in Alzheimer's Disease, Neurobiol Aging, 27(1):1359-1371 (2006).
Ekinci et al., "Hyperactivation of Mitogen-Activated Protein Kinase Increases Phospho-Tau Immunoreactivity Within Human Neuroblastoma: Additive and Synergistic Influence of Alteration of Additional Kinase Activities," Cell Mol. Neurobiol., 19(2):249-260 (1999).
El-Dahr et al., "Bradykinin Stimulates the ERKfwdanwElk-1fwdanwFos/AP-1 Pathway in Nesagial Cells," American Journal of Pyschology, 275(3 Part w):F343-F352 (Sep. 1998).
English-language Translation for JP 6-279311 dated Jun. 2008.
English-language Translation for JP10-90263 dated Apr. 10, 1998.
Etchberrigaray et al., "Ionic and Signal Transduction Alterations in Alzheimer's Disease," Molecular Neurobiology, 20 (1999).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).
Etcheberrigaray et al., "Calcium Responses in Fibroblasts from Asymptomatic Members of Alzheimer's Disease Families," Neurobiol. of Disease., 5:37-45 (1998).
Etcheberrigaray et al., "Potassium Channel Dysfunction in Fibroblasts Identifies Patients with Alzheimer Disease," Proc. Natl. Acad. Sci. USA, 90:8209-8213 (Sep. 1993).
Etcheberrigaray et al., "Therapeutic effects of PKC activators in Alzheimer's disease transgenic mice", PNAS, 01(30):11141-11146 (2004).
Etcheberrigary et al., "Molecular Mechanisms of Memory and the Pathophysiology of Alzheimer's Disease," Ann NY Acad Sci., 747:245-55 (1994).
European Search Report for EP 02 72 3236 dated Mar. 24, 2004.
Fan et al., "Arachidonic Acid and Related Methyl Ester Mediate Protein Kinase C Activation in Intact Platelets Through the Arachidonate Metabolism Pathways," Biochemical and Biophysical Research Communications, 169(3):933-940 (Jun. 29, 1990).
Favit et al., "Alzheimer's-specific effects of soluble β-amyloid on protein kinase C-and—degradation in human fybroblasts", Cell Biology, 95:5562-5567 (1998).
Frey et al. "Problems Associated with Biological Markers of Alzheimer's Disease," Neurochemical Research, 30(12):1501-1510 (Dec. 2005).
Gasparini et al., "Stimulation of β-Amyloid Precursor Trafficking by Insulin Reduces Intraneuronal β-Amyloid and Requires Mitogen-Activated Protein Kinase Signaling," The Journal of Neuroscience, 21(8):2561-2570 (Apr. 15, 2001).

(56) References Cited

OTHER PUBLICATIONS

Gebreyesus et al., "Bradykinin Elevates Tyrosine Hydroxylase and Dopamine Beta-Hydroxylase mRNA levels in PC12 Cells," Brain Research, 608(2):345-348 (1993).
Gibson et al., "Calcium stores in cultured fibroblasts and their changes with Alzheimer's disease," Biochimica et Biophysica Acta, 1316:71-77 (1996).
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Govoni et al., "Cytosol Protein Kinase C Downregulation in Fibroblasts from Alzheimer's Disease Patients," Neurology, 43:2581-2586 (1993).
Grant et al., "Phosphorylation of Mitogen-Activated Protein Kinase is Altered in Neuroectoderman Cells Overexpressing the Human Amyloid Precursor Protein 751 Isoform," Molecular Brain Research., 72:115-120 (1999).
Greenberg et al., "Secreted Beta-amyloid Precursor Protein Stimulates Mitogen-activated Protein Kinase and Enhances Tau Phosphorylation," Proc Natl Acad Sci USA, 91:7104-7108 (1994).
Growdon et al., "Biomarkers of Alzheimer Disease", Arch Neurol., vol. 56, No. 3, pp. 281-283, 1999.
Haug et al., "Decreased Inositol (1,4,5)-Trisphosphate Receptor Levels in Alzheimer's Disease Cerebral Cortex: Selectivity of Changes and Possible Correlation to Pathological Severity," Neurodegeneration, 5:169-176 (1996).
Heid, C.A. et al., "Real Time Quantitative PCR Genome" Res. 6, 986-994 (1996).
Hetman et al., "Role of Extracellular Signal Regulated Kinases 1 and 2 in Neuronal Survival," Eur. J. Biochem, 271:2050-2055 (2004).
Hirashima et al., "Calcium Responses in Human Fibroblasts: A Diagnostic Molecular Profile for Alzheimer's Disease," Neurology of Aging, 17(4):549-555 (1996).
Hogervorst et al., "The Validity and Reliability of 6 Sets of Clinical Criteria to Classify Alzheimer's Disease and Vascular Dementia in Cases confirmed Post-Mortem: Added Value of a Decision Tree Approach," Dement Geriatr Coqn Disord 2003:16:170-180.
Hongpaisan et al., "A structural basis for enhancement of long-term associative memory in single dendritic spines regulated by PKC", Proc. Natl. Acad. Sci .USA, vol. 104, No. 49, pp. 19571-19576, Dec. 4, 2007.
Huang et al., "Increased Inositol 1,4, 5-Trisphosphate Accumulation Correlates Withan Up-Regulation of Bradykinin Receptors in Alzheimer's Disease," Journal of Neurochemistry, 64(2):761-766 (Feb. 1995).
Huang et al., "Inositol Phosphates and Intracellular Calcium after Bradykinin Stilumation in Fibroblasts from Young, Normal Aged and Alzheimer Donors," Neurobiology of Aging, US, 12(5):469-473 (Sep. 1991).
Huynh et al., "Reduced Protein Kinase C Immunoreactivity and Altered Protein Phosphorylation in Alzheimer's Disease Fibroblasts," Arch Neurol 46 (1989).
Hyman et al.,, "Extracellular Signal-Regulated Kinase (MAP Kinase) Immunoreactivity in the Rhesus Monkey Brain." Neuroscience Letters, 166:113-116 (1994).
Irizarry et al., "Biomarkers of Alzheimer Disease in Plasma," The Journal of the American Society for Experimental NeuroTherapeutics, 1:226-234 (Apr. 2004).
Ito et al., "Internal Ca2+ Mobilization is Altered in Fibroblasts from Patients with Alzheimer Disease." Proc Natl Acad Sci USA, 91:534-538 (1994).
Jin et al., "Changes in Protein Kinases in Brain Aging and Alzheimer's Disease," Drugs &Aging, 6(2):136-149 (1995).
Kanno et al., "The Linoleic Acid Derivative DCP-LA Selectively Activates PKC-ϵ, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ϵ", Dept. of Physiology, Hyogo College of Med., Hyogo, Japan, p. 552 (2006).
Khan et al., "A Cellular Model of Alzheimer's Disease Therapeutic Efficacy: PKC Activation Reverses a Beta-Induced Biomarker Abnormality on Cultured Fibroblasts," Neurobiology of Disease, 34(2): 332-339, vol. 34, No. 2 (May 2009).
Khan et al., "An Internally Controlled Perifpheral Biomarker for Alzheimer's Disease: Erk1 and Erk2 responses to the Inflammatory Signal Bradykinin," PNAS, vol. 103, No. 35, pp. 13203-13207, Aug. 29, 2006.
Kilpatrick et al., "Regulation of TNF Mediated Antiapoptoptic Signaling in Human Neutrophils: Role of -PKC and ERK1/2," Journal of Leukocyte Biology, 80:1512-1521 (Dec. 2006).
Kurumatani et al., "Loss of Inositol 1,4,5-trisphosphate Receptor Sites and Decreased PKC Levels Correlate with Staging of Alzheimer's Disease Neurofibrillary Pathology," Brain Research, 796:209-221 (1998).
Laporte et al., "Role of ERK MAP Kinases in Responses of Cultured Human Airway Smooth Muscles Cells to IL-1B." Am. J. Physiol. Lung Cell Mol. Physiol., 277:943-951 (1999).
Leissring et al., "Capacitative Calcium Entry Deficits and Elevated Luminal Calcium Content in Mutant Presenilin-1 Knockin Mice," The Journal of Cell Biology, 149 (2000).
Leissring et al., "Presenilin-2 Mutations Modulate Amplitude and Kinetics of Inositol 1,4,5-Trisphosphate-mediated Calcium Signals," The Journal of Biological Chemistry, 274(46):32535-32538 (Nov. 12, 1999).
Liang et al., "Altered Neuronal Gene Expression in Brain Regions Differentially affected by Alzheimer's Disease: A reference Data Chart," Physiol Genormics, 33:240-256 (2008).
Loring et al., "A Gene Expression Profile of Alzheimer's Disease," DNA and Cell Biology, 20(11):683-695 (2001).
Lu et al., P44mpk MAP Kinase Induces Alzheimer Type Alterations in Tau Function and in Primary Hippocampal Neurons, J. Neurosci. Res., 35:439-444 (1993).
Luigi et al., "Inflammatory Markers in Alzheimer's Disease and Multi-Infarct Dementia," Mechanisms of Ageing and Development, 122:1985-1995 (2001).
Masliah, "Differential Involvement of Protein Kinase C Isozymes in Alzheimer's Disease," Journal of Neuroscience, 10:2113-2124 (1990).
Masliah, "Protein Kinase C Alteration Is an Early Biochemical Marker in Alzheimer's Disease," The Journal of Neuroscience, 11(9): 2759-2767 (1991).
Mattson et al., "Presenilin-1 Mutation Increases Neuronal Vulnerability to Focal Ischemia in Vivo and to Hypoxia and Glucose Deprivation in Cell Culture: Involvement of Perturbed Calcium Homeostatis," The Journal of Neuroscience, 20(4):1358-1364 (Feb. 15, 2000).
McDonald et al., "β-Amyloid Fibrils Activate Parallel Mitogen-Activated Protein Kinase Pathways in Microglia and THP1 Monocytes," J Neurosci, 18:4451-4460 (1998).
Nagasaka et al., "A Unique Gene Expression Signature Discriminates Familial Alzheimer's Disease Mutation Carriers from their Wild-type Siblings,", Proc. Natl. Acad. Sci., 102(41):14854-14859 (2005).
Nagata et al., "FR236924, a Newly Synthesized Derivataive of Linoleic Acid, Ameliorates Memory Deficits in Rats Intraventricularly Injected with Amyloid-Beta Peptide." Jpn. J. Physiol. 53,Suppl. 2003(319): S261.
Nagata et al., "The Newly Synthesized Linoleic Acid Derivative CP-LA Ameliorates Memory Deficits in Animal Dmodels Treated with Amyloid-β Peptide and Scopolamine", Psychogeriatrics, 5:22-126 (2003).
Neve et al., "Alzheimer's Disease: Dysfunction of a Signaling Pathway Mediated by the Amyloid Precursor Protein?" Biochem. Soc. Symp. 67:37-50, (2001).
Ning et al., "Early Response Gene Signaling in Bryostatin-Stimulated Primary B Chronic Lymphocytic Leukaemia Cells in Vitro," Biochemical Journal, 319(1):59-65 (1996).
NME Digest, Drug News Perspect, 2002, pp. 666-674, vol. 15, No. 10.

(56) References Cited

OTHER PUBLICATIONS

Oddo et al., "Temporal Profile of Amyloid-β (AB) Oligomerization in an in Vivo Model of Alzheimer Disease—A Link Between AB and TAU Pathlogy," Journal of Biological Chemistry, 281(3):1599-1604 (Jan. 20, 2006).
Ohta et al., "Stearic Acid Facilities Hoppocampal Neurotransmission by Enhancing Micotinic Ach Receptor Responses via an PKC Pathway," Molecular Brain Research, 119:83-89 (Aug. 27, 2003).
Pascale et al., "Enhanced BK-Induced Calcium Responsiveness in PC12 Cells Expressing the C100 Fragment of the Amyloid Precursor Protein," Brain Res Mol Brain Res, 72:205-2 (1999).
Pub Chem Compound, XP002550143 (May 27, 2005).
Putney, Jr., "Presenilins, Alzheimer's Disease, and Capacitative Calcium Entry," Neuro, 27:411-412 (2000).
Racchi et al., "Bradykinin-induced amyloid precursor protein secretion: a protein kinase C-independent mechanism that is not altered in fibroblasts from patients with sporadic Alzheimer's disease", Biochem J., vol. 330, pp. 1271-1275, 1998.
Rapoport et al., "PD98059 Prevents Neurite Degeneration Induced by Fibrillar B-Amyloid in Mature Hippocampal Neurons", J. Neurochem., vol. 74, pp. 125-133, 2000.
Remarque et al., "Patients with Alzheimer's Disease Display a Pro-inflammoatory Phenotype," Experimental Gerontology, 36:171-176 (2001).
Reynolds et al., "Phosphorylation Sites on Tau Identified by Nanoelectrospray Mass Spectrometry:Differences in Vitro Between the Mitogen-Activated Protein Kinase ERK2, c-Jun N-Terminal Kinase and 0P38, and Glycogen Synthase Kinase-3B," J. Neurochem., 74:1587-1595 (2000).
Roux et al., ""ERK and p38 MAPK-Activated Protein Kinases: a Family of Protein Kinase with Diverse Biological Functions, Microbiology and Molecular Biology Reviews, 68(2):320-344 (Jun. 2004).
Sato et al., "Elevated Amyloid Beta Protein (1-40) Level Induces CREB Phosphorylation at Serine-133 via p44/42 MAP kinase (Erk1/2)-dependent pathway in rat pheochromocytoma PC12 cells," Biochemical and Biophysical Research Communications, 232(3):637-642(Mar. 27 1997).
Sheehan et al., "Calcium Homeostasis and Reactive Oxygen Species Production in Cells Transformed by Mitochondria from Individuals with Sporadic Alzheimer's Disease," The Journal of Neuroscience, 17(12):4612-4622 (Jun. 15, 1997).
Sun et al., "Poststroke neuronal rescue and synaptogenesis mediated in vivo by protein kinase C in adult brains", Proc. Natl. Acad. Sci. USA, Sep. 9, 2008; vol. 105, No. 36, pp. 13620-13625.
Sun et al., "Dual Effects of Bryostatin-1 on Spatial Memory and Depression", Eur. J. Pharmacol., vol. 512, pp. 43-51, 2005.
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "The Gene Defects Responsible for Familial Alzheimer's Disease," Neurolobiology of Disease, 3:159-168 (1996).
Thal et al., "The Role of Biomarkers in Clinical Trials for Alzheimer Disease," Alzheimer Dis Assoc Disord, 20(1) Jan.-Mar. 2006.
Yaguchi et al., "Effects of Cis-unsaturated Free Fatty Acids on PKC-ε Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Yang et al., "Bradykinin-Induced p42/p44 MAPK Phosphorylation and Cell Proliferation via Src, EGF Receptors and P13-K/Akt in Vascular Smooth Muscle Cells," Journal of Cellular Physiology, 203:538-546 (2005).
Yoo et al., "Presenilin-Mediated Modulation of Capacitative Calcium Entry," Neuron, 27:561-572 (Sep. 2000).
Youdim et al., "Molecular Basis of Neuroprotective Activities of Rasagiline and the Anti-Alzheimer Drug TV3326 [(N-Propargyl-(3R)Aminoindan-5-YL)-Ethyl Methyl Carbamate]," Cellular and Molecular Neurobiology, 21(6): 555-573 (Dec. 2001).
Young, et al., "Decreased Brain [3H]inositol 1 ,4,5-trisphosphate Binding in Alzheimer's Disease," Neuroscience Letters, 94:198-202 (2000).
Zhang et al., "Oxidative Stress Differentially Modulates Phosphorylation of ERK, p38 and CREB Induced by NGF or EGF in PC12 Cells." Neurobiology of Aging, 20:271-278 (1999).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Zhao et al., "Dysfunction of MAP Kinase signaling in Alzheimer's Disease," Society of Neuroscience, Abstracts 25, 31st Annual Meeting of the Society of Neuroscience, San Diego, CA, USA, 27(1):924, (Nov. 10-15, 2001).
Zhao et al., "Impairment of Phosphatase 2A Contributes to the Prolonged MAP Kinase Phosphorylation in Alzheimer's Disease Fibroblasts," Neurobiology of Disease, 14(3):458-469 (Dec. 2003).
Zhao et al., "MAP Kinase Signaling Cascade Dysfunction Specific to Alzheimer's Disease in Fibroblasts," Neurobiology of Disease, 11(1):166-183 (Oct. 2002).
Blobe et al., "Regulation of protein kinase C and role in cancer biology," Cancer Metast. Rev. 1994; 13;411-431.
Extended European Search Report in EP 13004274.0 dated Oct. 28, 2013.
Huang et al., "Involvement of Intermediary Metabolites in the Pathway of Extracellular Ca2+ Induced Mitogen-Activated Protein Kinase Activation in Human Fibroblastes," Cell, Signal, vol. 11, No. 4, pp. 263-274 (1999).
Hug et al., "Protein kinase C isoenzymes: divergence in signal transduction?" Biochem J. 1993; 291:329-343.
International Preliminary Report on Patentability and Written Opinion for PCT/2005/036014 dated Apr. 24, 2008.
International Preliminary Report on Patentability and Written Opinion for PCT/2006/022156 dated Apr. 24, 2008.
International Preliminary Report on Patentability and Written Opinion for PCT/US2006/037186 dated Apr. 16, 2008.
International Search Report and Written Opinion for PCT/US2006/037186 dated Apr. 11, 2007.
International Search Report issued on PCT/US2005/036014, dated Apr. 19, 2007.
International Search Report issued on PCT/US2006/022156, dated Apr. 19, 2007, 6 pages.
Liu et al., "The Sevenfold Way of PKC Regulation," Cellular Signaling, 10(8):529-42 (1998).
Office Action dated Aug. 24, 2012, in U.S. Appl. No. 12/083,056.
Office Action dated Oct. 11, 2012, U.S. Appl. No. 12/896,862.
Office Action dated Sep. 20, 2012, im U.S. Appl. No. 12/729,042.
Office Action dated Apr. 29, 2011, in U.S. Appl. No. 12/083,086.
Office Action dated Aug. 17, 2012, in U.S. Appl. No. 11/660,868.
Office Action dated Nov. 15, 2012, in U.S. Appl. No. 12/510,707.
Office Actino (Final) dated Sep. 13, 2011, in U.S. Appl. No. 11/660,868.
Office Action (Final) dated Oct. 11, 2011, in U.S. Appl. No. 12/083,056.
Office Actino (Restriction Requirement) dated Dec. 2, 2010, in U.S. Appl. No. 12/083,056.
Office Action (Final) dated May 19, 2015 in U.S. Appl. No. 12/895,957.
Office Action (Final) dated Oct. 17, 2013, in U.S. Appl. No. 12/729,042.
Office Action dated Jan. 2, 2014, in U.S. Appl. No. 12/729,042.
Office Action dated Mar. 25, 2014, in U.S. Appl. No. 12/895,957.
Office Action (Final) dated Jun. 13, 2014 in U.S. Appl. No. 13/401,459.
Office Action (non-final) dated Nov. 5, 2014, in co-pending U.S. Appl. No. 12/895,957.

(56) References Cited

OTHER PUBLICATIONS

Office Action dated Aug. 2, 2013, U.S. Appl. No. 12/510,707.
Office Action dated Jul. 31, 2013, in U.S. Appl. No. 13/401,459.
Office Action dated Nov. 18, 2013, in U.S. Appl. No. 12/895,957.
Silverstein, A.M. et al., "Actions of PP2A on the MAP Kinase Pathway and Apoptosis are Mediated by Distinct Regulatory Subunits", Proc. Natl. Acad. Sci. USA 99,4221-4226 (2002).
Office Action dated Feb. 12, 2016, in U.S. Appl. No. 12/895,957.
Office Action dated Jan. 18, 2017, in U.S. Appl. No. 12/895,957.
Office Action dated Dec. 9, 2016, U.S. Appl. No. 14/803,762.

\* cited by examiner

ALZHEIMER'S DISEASE-SPECIFIC ALTERATIONS OF THE ERK1/ERK2 PHOSPHORYLATION RATIO-ALZHEIMER'S DISEASE-SPECIFIC MOLECULAR BIOMARKERS (ADSMB)

This is a continuation of application Ser. No. 12/083,056, filed Aug. 29, 2008, which is a national stage entry under 35 U.S.C. §371 of International Application No. PCT/US2006/037186 filed Sep. 25, 2006, which is a continuation-in-part of International Application PCT/US2006/022156 filed on Jun. 7, 2006, which is a continuation-in-part of International Application No. PCT/US2005/036014 filed Oct. 11, 2005 and U.S. application Ser. No. 11/246,524 filed Oct. 11, 2005, now U.S. Pat. No. 7,595,167 issued on Sep. 29, 2009, the disclosures of which are hereby incorporated by reference in their entireties.

FIELD OF THE INVENTION

The present invention relates to methods of diagnosing Alzheimer's Disease or confirming the presence or absence of Alzheimer's Disease in a subject. The present invention also relates to methods of screening for lead compounds that may be used for the development of therapeutic agents useful in treating or preventing Alzheimer's Disease. The invention also relates to methods of diagnosing Alzheimer's Disease in a subject by detecting alterations in the ratio of specific phosphorylated MAP kinase proteins in cells after stimulation with a protein kinase C activator. The Alzheimer's Disease-Specific Molecular Biomarkers (ADSMB) disclosed herein are useful for the diagnosis of Alzheimer's Disease, for monitoring disease progression and in screening methods for the identification of lead compounds.

BACKGROUND OF THE INVENTION

Perturbation of intracellular calcium homeostasis, increased levels of oxidative stress, and inflammatory mechanisms resulting in excitatory toxicity and neuronal death have been suggested to contribute to the pathogenesis of Alzheimer's Disease (AD) (Ito et al. 1994, Putney, 2000; Yoo et al., 2000; Sheehan et al., 1997; De Luigi et al., 2001; Anderson et al., 2001; Remarque et al, 2001). A number of AD-associated abnormalities in intracellular $Ca^{2+}$ levels and other cellular processes have derived from studies using bradykinin as a stimulus. As a potent inflammation mediator, bradykinin (BK) is produced by brain and peripheral cells under patho-physiological conditions such as trauma, stroke, pain ischemia, and asthma (Regoli et al., 1993; Bockmann & Paegelow, 2000; Ellis et al., 1989; Kamiya et al., 1993). By acting on the B2 bradykinin receptor (BK2bR), a G-protein-coupled receptor, BK triggers phosphatldylinositol (PI) turnover through activity of phospholipase C (PLC), which in turn produces inositol 1,4,5-trisphospate (IP3) that increases intracellular $Ca^{2+}$ release from the IP3-sensitive stores (Noda et al., 1996; Venema et al., 1998; Wassdal et al., 1999; Cruzblanca et al., 1998; Ricupero et al., 1997; Pascale et al., 1999). Through the same pathway, BK also triggers production of other proinflammatory cytokines through activation of mitogen-activated protein (MAP) kinases (Hayashi et al., 2000; Schwaninger et al., 1999; Phagoo et al., 2001). Enhanced elevation of intracellular $Ca^{2+}$ levels has been found in AD brains as well as in AD peripheral cells in response to stimulation of bradykinin and inactivation of $K^+$ channels (Etcheberrigaray et al., 1993, 1998; Hirashima et al., 1996; Gibson et al., 1996(a)).

Stimulation of PLC subsequent to BK2bR activation also leads to production of diacylglycerol which, along with increased intracellular $Ca^{2+}$, activates protein kinase C (PKC) isoforms. The BK-activated PLC/phospholipids-$Ca^{2+}$/PKC cascade interacts with the Ras/Raf signaling pathway, which activates extracellular signal-regulated kinases 1/2 (Erk 1 and Ezk2, which are referred to together as "Erk1/2"), a subtype of the MAP kinase family (Berridge, 1984; BAssa et al., 1999; Hayashi et al., 2000; Blaukat et al., 2000, Zhao et al. Neurobiology of Disease 11, 166-183, 2002). Erk1/2 receives signals from multiple signal transduction pathways and leads to cellular proliferation and differentiation by regulation of gene expression through a number of transcriptional factors, including AP-1, NF-κB, and cyclic AMP-responsive element binding protein (CREB). By acting as one of the major kinases, Erk2 phosphorylates tau at multiple serine/threonine sites including Ser-262 and Ser-356 (Reynolds et al., 1993; Lu et al., 1993). In addition, PKC-activated MAP kinase and BK receptor-associated pathways have been shown to regulate formation and secretion of the soluble form of amyloid precursor protein (sAPP) by different laboratories (Desdouits-Magnen et al., 1998; Gasparini et al., 2001; Nitsch et al., 1994, 1995, 1996, 1998). These findings have suggested the possibility that BK-associated sAPP processing may be linked to the PKC-MAP kinase pathway. On the other hand, pathological conditions such as viral infections, increased oxidative stress, aberrant expression of APP, and exposure to APβ cause activation of MAP kinase (Rodems & Spector, 1998; McDonald et al., 1998; Ekinci et al., 1999; Grant et al., 1999) and enhanced tau phosphorylation (Greenberg et al., 1994; Ekinci & Shea, 1999; Knowles et al., 1999). These effects implicate derangement of a MAP kinase signaling pathway(s) in the pathogenesis of AD.

Mitogen-activated protein kinases (such as Erk1 and Erk2) regulate phosphorylation of the microtubule associated protein tau and processing of the amyloid protein β, both events critical to the pathophysiology of Alzheimer's disease. Enhanced and prolonged Erk1/2 phosphorylation in response to bradykinin has been detected in fibroblasts of both familial and sporadic Alzheimer's Disease, but not age-matched controls (Zhao et al. Neurobiology of Disease 11, 166-183, 2002). Sustained Erk1/2 phosphorylation induced by bradykinin has previously been found in Alzheimer's Disease fibroblasts and is the subject of WO 02/067764, which is herein incorporated by reference in its entirety.

There exists a need for highly sensitive and highly specific tests to diagnose Alzheimer's Disease and to screen for compounds useful in the treatment and prevention of Alzheimer's Disease. The present inventors have identified, for the first time, unique Alzheimer's Disease-specific molecular biomarkers useful for the diagnosis of Alzheimer's Disease in a highly sensitive and highly specific manner compared to previously known diagnostic tests. Thus, the unique Alzheimer's Disease-specific molecular biomarkers disclosed herein serve as the basis for diagnostic methods having a high degree of sensitivity and specificity for the detection and diagnosis of Alzheimer's Disease. The unique Alzheimer's Disease-specific molecular biomarkers of the present invention are also useful in screening methods to identify compounds which may be used as therapeutic agents in the treatment and prevention of Alzheimer's Disease.

SUMMARY OF THE INVENTION

The present invention is directed to methods for determining or confirming the presence or absence of Alzheimer's Disease in a subject. In certain embodiments, the methods comprise contacting cells from a subject with an amyloid beta peptide and determining whether said contacting step induces an Alzheimer's Disease phenotype in said cells; wherein the absence of Alzheimer's Disease in said subject is established or indicated if an Alzheimer's Disease phenotype is induced in said cells by said contacting step. In certain embodiments, the presence of Alzheimer's Disease in said subject is established or indicated if incubation with said amyloid beta peptide results in no significant alteration or change in an Alzheimer's Disease phenotype in said cells. No significant alteration or change in an Alzheimer's Disease phenotype means that the value of an Alzheimer's Disease-specific molecular biomarker is unchanged compared to its value before the cells are contacted with said amyloid beta peptide, or the value of said Alzheimer's Disease-specific molecular biomarker is changed or altered compared to its value before the cells are contacted with said amyloid beta peptide by less than about 15%, or less than about 14%, or less than about 13%, or less than about 12%, or less than about 11%, or less than about 10%, or less than about 9%, or less than about 8%, or less than about 7%, or less than about 6%, or less than about 5%, or less than about 4%, or less than about 3% or less than about 2%, or less than about 1% or less than about 0.5%, or less than about 0.25%.

In certain embodiments, the amyloid beta peptide is Aβ (1-42), although any amyloid beta peptide may be used. In further embodiments, the methods comprise contacting said cells with a protein kinase C activator. In still further embodiments, said protein kinase C activator is selected from the group consisting of bradykinin, bryostatin, bombesin, cholecystokinin, thrombin, prostaglandin F2α and vasopressin. In still further embodiments, said cells are peripheral cells. In still further embodiments, said cells are selected from the group consisting of fibroblasts, saliva, blood, urine, skin cells, buccal mucosa cells and cerebro spinal fluid. All of the methods described herein may be performed in vivo or in vitro. In preferred embodiments, the methods of the present invention are performed in vitro.

In certain embodiments of the present invention, the Alzheimer's Disease phenotype is induced in said cells if the value of an Alzheimer's Disease-specific molecular biomarker is a positive value greater than zero.

A preferred embodiment of the present invention is directed to a method for determining or confirming the absence of Alzheimer's Disease in a subject comprising contacting cells from a subject with Aβ (1-42); contacting said cells with bradykinin; measuring the value of an Alzheimer's Disease-specific molecular biomarker, wherein the absence of Alzheimer's Disease in said subject is established or indicated if the value of said Alzheimer's Disease-specific molecular biomarker is a positive value greater than zero. In certain embodiments, the presence of Alzheimer's Disease in said subject is established or indicated if incubation with said amyloid beta peptide results in no significant alteration or change in an Alzheimer's Disease phenotype in said cells. No significant alteration or change in an Alzheimer's Disease phenotype means that the value of an Alzheimer's Disease-specific molecular biomarker is unchanged compared to its value before the cells are contacted with said amyloid beta peptide, or the value of said Alzheimer's Disease-specific molecular biomarker is changed or altered compared to its value before the cells are contacted with said amyloid beta peptide by less than about 15%, or less than about 14%, or less than about 13%, or less than about 12%, or less than about 11%, or less than about 10%, or less than about 9%, or less than about 8%, or less than about 7%, or less than about 6%, or less than about 5%, or less than about 4%, or less than about 3% or less than about 2%, or less than about 1% or less than about 0.5%, or less than about 0.25%. In a still further preferred embodiment, said cells are peripheral cells. In a still further preferred embodiment said cells are selected from the group consisting of fibroblasts, saliva, blood, urine, skin cells, buccal mucosa cells and cerebro spinal fluid The present invention is also directed to methods for identifying a lead compound useful for the treatment of Alzheimer's Disease comprising the steps of contacting non-Alzheimer's cells with an amyloid beta peptide, contacting the same cells with an agent that is a protein kinase C activator, further contacting the cells with a test compound, and determining the value of an Alzheimer's Disease-specific molecular biomarker.

In one embodiment of the present invention, the amyloid beta peptide is Aβ (1-42) although any amyloid beta peptide may be used. In another embodiment of the present invention, the non-Alzheimer's cells are selected from a group consisting of fibroblasts, saliva, blood, urine, skin cells, buccal mucosa cells, and cerebro spinal fluid. In yet another embodiment of the present invention, the protein kinase C activator is selected from the group consisting of bradykinin, bryostatin, bombesin, cholecystokinin, thrombin, prostaglandin F2α and vasopressin.

In certain embodiments of the present invention, the value of an Alzheimer's Disease-specific molecular biomarker is indicative a compound that is useful for the treatment of Alzheimer's Disease if the value of the Alzheimer's Disease-specific molecular biomarker is less than the value of a similar molecular biomarker measured from control cells that have not been contacted with the test compound. In preferred embodiments, the control cells have been contacted with an amyloid beta peptide. In other preferred embodiments, the amyloid beta peptide is Aβ (1-42) although any amyloid beta peptide may be used. In still other preferred embodiments, the control cells have been contacted with an agent that is a protein kinase C activator.

In certain embodiments, the method for identifying a lead compound useful for the treatment of Alzheimer's Disease further comprises the step of modifying the compound identified as being useful for the treatment of Alzheimer's Disease to optimize or improve its safety and efficacy compared to the safety and efficacy of an unmodified compound. In a preferred embodiment, the modified compound identified is useful for the treatment of Alzheimer's disease.

The invention also discloses a method of treating Alzheimer's Disease, comprising administering a therapeutically effective amount of the modified compound, to a subject in need thereof.

The present invention also is directed to a method of identifying a compound useful for the treatment of Alzheimer's Disease comprising contacting non-Alzheimer's control cells with Aβ (1-42) although any amyloid beta peptide may be used, contacting the same control cells with bradykinin, further contacting the control cells with a test compound, and determining the value of an Alzheimer's Disease-specific molecular biomarker to identify a compound useful for the treatment of Alzheimer's Disease.

The present invention is directed, in certain embodiments, to methods of diagnosing Alzheimer's Disease in a subject comprising the steps of contacting cells obtained from a subject with an agent that is a protein kinase C activator and measuring the ratio of specific phosphorylated MAP kinase proteins in the cells to diagnose Alzheimer's Disease in the subject. In a preferred embodiment, the ratio of specific phosphorylated MAP kinase proteins is a ratio between two phosphorylated MAP kinase proteins. In preferred embodiments, the diagnostic methods of the invention comprise an in vitro assay. In still further preferred embodiments of the diagnostic methods, the specific phosphorylated MAP kinase proteins are sequence variants of each other and belong to the same family of proteins.

In certain embodiments of the invention, the ratio of specific phosphorylated MAP kinase proteins is the ratio of phosphorylated Erk1 to phosphorylated Erk2 and is calculated by dividing the normalized amount of phosphorylated Erk1 by the normalized amount of phosphorylated Erk2. In preferred embodiments of the invention, the protein kinase C activator is selected from the group consisting of bradykinin, bryostatin, bombesin, cholecystokinin, thrombin, prostaglandin F2α and vasopressin.

In certain embodiments of the invention, the cells that are used in the diagnostic assays are peripheral cells. In preferred embodiments, the cells may be skin cells, skin fibroblast cells, blood cells or buccal mucosa cells. In certain embodiments, the cells are not isolated from cerebral spinal fluid. In other preferred embodiments, the cells do not comprise cerebral spinal fluid. In still other preferred embodiments, the cells are not obtained by a spinal tap or lumber puncture.

In certain embodiments of the diagnostic methods, a protein kinase C activator is contacted with cells in media comprising serum. In other preferred embodiments of the invention, a protein kinase C activator is contacted with said cells in serum-free media.

In certain embodiments of the diagnostic methods of the invention, phosphorylated MAP kinase proteins are detected by immunoassay. In preferred embodiments of the invention, the immunoassay may be a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay. In further preferred embodiments of the diagnostic methods of the invention, protein arrays or peptide arrays or protein micro arrays may be employed in the diagnostic methods.

In certain embodiments, when a negative diagnosis of Alzheimer's Disease is achieved or indicated (i.e. the absence or lack of results indicating the presence of Alzheimer's Disease) using any of the diagnostic methods disclosed herein, a further, confirmatory diagnostic method may be performed using the diagnostic methods disclosed herein directed to determining the absence of Alzheimer's Disease. Such a confirmatory diagnostic method may be performed in parallel with or subsequent to any of the diagnostic methods disclosed herein. Similarly, when a positive diagnosis of Alzheimer's Disease is indicated, (i.e. results indicating the presence of Alzheimer's Disease) using any of the diagnostic methods disclosed herein, a further, confirmatory diagnostic method may be performed using the diagnostic methods disclosed herein directed to determining the presence of Alzheimer's Disease. Such a confirmatory diagnostic method may be performed in parallel with or subsequent to any of the diagnostic methods disclosed herein.

In certain embodiments of the diagnostic methods of the invention, Alzheimer's Disease may be diagnosed in a subject by contacting cells from the subject with an agent that is a protein kinase C activator and then measuring the ratio of a phosphorylated first MAP kinase protein to a phosphorylated second MAP kinase protein, wherein the phosphorylated first and phosphorylated second MAP kinase proteins are obtained from the cells after they have been contacted with the protein kinase C activator. In further embodiments of the diagnostic methods of the invention, the ratio of phosphorylated first MAP kinase protein to phosphorylated second MAP kinase protein in cells in the subject that have not been contacted with the protein kinase C activator is determined and this ratio is subtracted from the ratio of phosphorylated first and second MAP kinase proteins obtained from cells after they have been contacted with the protein kinase C activator to diagnose the presence of Alzheimer's Disease in the subject based on the difference in the ratios. In preferred embodiments of the diagnostic methods of the invention, the difference in the ratios is diagnostic of Alzheimer's Disease in the subject if the difference is a positive value.

In other preferred embodiments of the diagnostic methods of the invention, said difference is diagnostic of the absence of Alzheimer's Disease in the subject if the difference is a negative value or zero.

Certain embodiments of the invention are directed to kits for diagnosing Alzheimer's Disease in a subject. In certain embodiments of the invention, the kit may contain an agent that is a protein kinase C activator, in further embodiments of the invention, the kits may contain an antibody specific for a phosphorylated first MAP kinase protein. In still further embodiments of the invention, the kits may contain an antibody specific for a phosphorylated second MAP kinase protein. In preferred embodiments, the kits may contain any combination of the foregoing.

In certain embodiments of the invention, the kits for diagnosing Alzheimer's Disease in a subject may contain one or more protein kinase C activators selected from the group consisting of bradykinin, bryostatin, bombesin, cholecystokinin, thrombin, prostaglandin F2α and vasopressin. In preferred embodiments, the kits may contain any combination of the foregoing.

In certain embodiments of the invention, the kits for diagnosing Alzheimer's Disease in a subject may contain antibodies specific for phosphorylated Erk1 or phosphorylated Ezk2 or both. In preferred embodiments of the invention, the kit may contain anti-phospho-Erk1 antibody. In further preferred embodiments of the invention, the kit may contain an anti-phospho-Erk2 antibody. In preferred embodiments, the kits may contain any combination of the foregoing.

In certain embodiments of the invention, the kits for diagnosing Alzheimer's Disease may further comprise an amyloid beta peptide. In certain preferred embodiments, the amyloid beta peptide may be Aβ (1-42).

In certain embodiments of the invention, the kits for diagnosing the presence or absence Alzheimer's Disease in a subject comprise an amyloid beta peptide; an antibody specific for a phosphorylated first MAP kinase protein; and an antibody specific for a phosphorylated second MAP kinase protein. In a preferred embodiment, the amyloid beta peptide is Aβ (1-42). In preferred embodiments, the kits may contain any combination of the foregoing.

Certain embodiments of the invention are directed to methods for screening a test compound (or a lead compound) useful for the treatment or prevention of Alzheimer's Disease comprising: contacting cells isolated from a subject diagnosed with Alzheimer's Disease with an agent that is a protein kinase C activator, wherein the contacting is done in the presence of the test compound (or a lead compound); measuring the ratio of a phosphorylated first MAP kinase protein to a phosphorylated second MAP kinase protein, wherein the phosphorylated first and phosphorylated second MAP kinase proteins are obtained from the cells after the contacting; measuring the ratio of phosphorylated first MAP kinase protein to phosphorylated second MAP kinase protein in cells from the subject that have not been contacted with the test compound (or a lead compound); subtracting the ratio obtained from the contacting step done in the absence of the test compound (or a lead compound) from the ratio obtained from the contacting step done in the presence of the test compound (or a lead compound); and identifying a test compound (or a lead compound) useful for the treatment of Alzheimer's Disease based on the difference in the ratios. In preferred embodiments of the methods for screening a test compound (or a lead compound) useful for the treatment or prevention of Alzheimer's Disease, the calculated difference in the ratios is indicative of a test compound (or a lead compound) useful for the treatment of Alzheimer's Disease if the difference is a negative value or zero.

In preferred embodiments, the invention is directed to methods for screening a test compound (or a lead compound) useful for the treatment or prevention of Alzheimer's Disease wherein the methods comprise an in vitro assay.

In preferred embodiments of the methods for screening a test compound (or a lead compound) useful for the treatment or prevention of Alzheimer's Disease, the first MAP kinase protein is Erk1 and the second MAP kinase protein is Erk2. In still further preferred embodiments of the invention, the ratios are calculated by dividing the normalized amount of phosphorylated Erk1 by the normalized amount of phosphorylated Erk2. In further embodiments of the invention, the protein kinase C activator is selected from the group consisting of bradykinin, bryostatin, bombesin, cholecystokinin, thrombin, prostaglandin F2α and vasopressin. In further embodiments of the invention, the cells are peripheral cells. In still further embodiments of the invention, the peripheral cells are selected from the group consisting of skin cells, skin fibroblast cells, blood cells and buccal mucosa cells. In still further embodiments of the invention, the cells are not isolated from cerebral spinal fluid. In still further embodiments of the invention, the cells do not comprise cerebral spinal fluid. In still further embodiments of the invention, the cells are not obtained by a spinal tap or lumbar puncture. In still further embodiments of the invention, the protein kinase C activator is contacted with said cells in media comprising serum. In still further embodiments of the invention, the protein kinase C activator is contacted with said cells in serum-free media. In still further embodiments of the invention, the phosphorylated MAP kinase proteins are detected by immunoassay. In still further embodiments of the invention, the immunoassay is a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay. In still further embodiments of the invention, the measuring is done using a protein array, a peptide array, or a protein micro array.

In certain embodiments, the invention is directed to methods of monitoring Alzheimer's Disease progression in a subject comprising measuring an Alzheimer's Disease-specific molecular biomarker. In certain preferred embodiments, the method comprises measuring the Alzheimer's Disease-specific molecular biomarker at more than one time point. In preferred embodiments, the Alzheimer's Disease-specific molecular biomarker is measured at time points separated by at least six months, more preferably, at time points separated by at least 12 months. In preferred embodiments of the invention, a decrease in the numerical value (i.e. a less positive value) of the Alzheimer's Disease-specific molecular biomarker is indicative of Alzheimer's Disease progression in said subject.

In certain embodiments, the invention is directed to compositions useful for the treatment of Alzheimer's Disease comprising a compound identified by any of the methods for screening compounds disclosed herein. In preferred embodiments, the compositions of the invention comprise a pharmaceutical composition for treating Alzheimer's Disease in a subject in need thereof comprising a therapeutically effective amount of a compound identified by any of the methods for screening compounds disclosed herein.

In certain embodiments, the present invention is directed to methods of treating Alzheimer's Disease comprising administering a therapeutically effective amount of any of the pharmaceutical compositions disclosed herein to a subject in need thereof.

DETAILED DESCRIPTION

Figure 1:
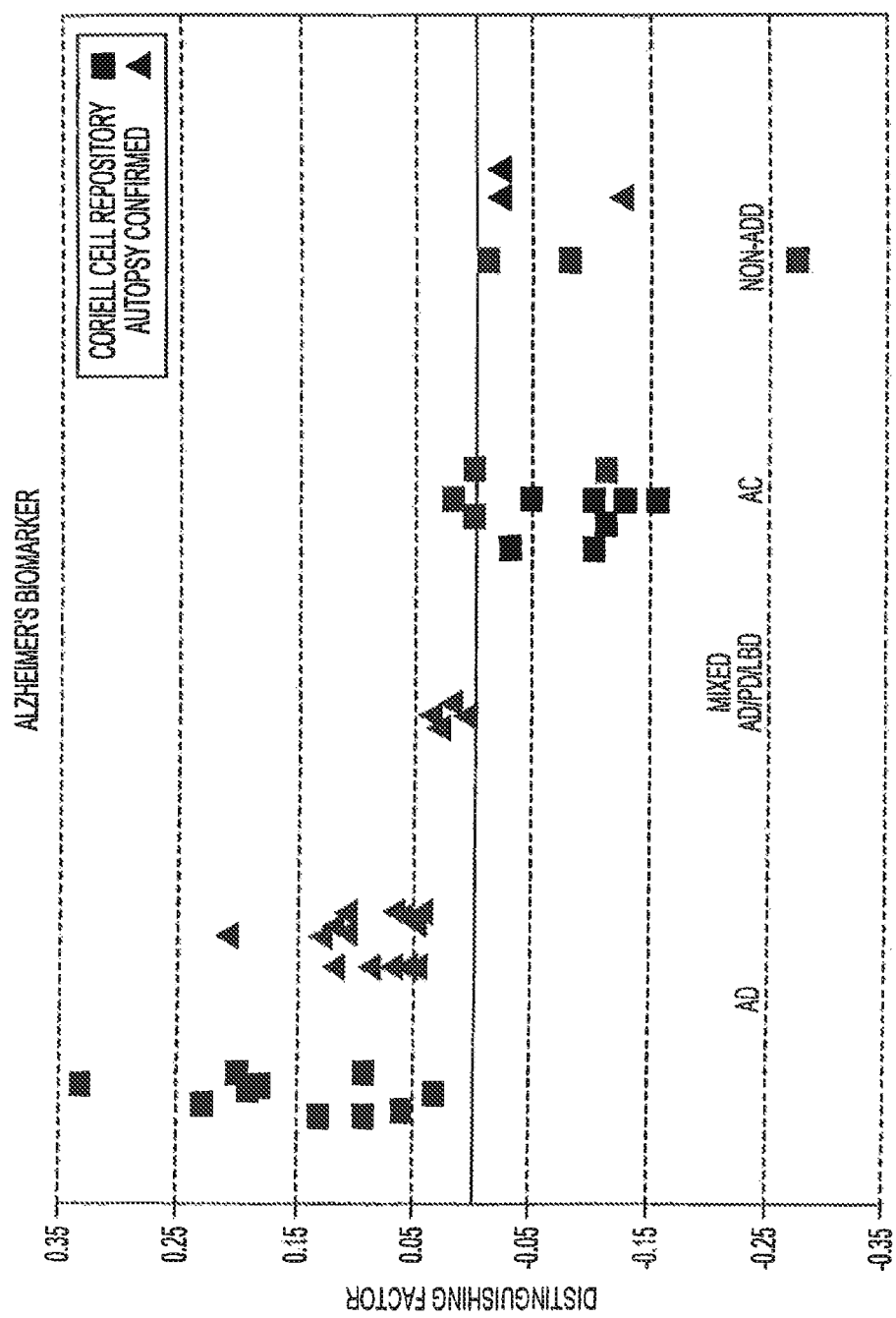
FIG. 1 shows the results of determinations of Alzheimer's Disease-specific molecular biomarkers (ADSMB) in banked skin fibroblast cells obtained from the Coriell Cell Repository and in punch skin biopsy samples that were immediately placed in tissue culture and which were obtained from Autopsy confirmed subjects. AD refers to Alzheimer's Disease cells; Mixed AD/PD/LBD refers to cells taken from patients with mixed pathologies of Alzheimer's Disease, Parkinson's Disease and/or Loewi Body disease; AC refers to non-dementia age-matched control cells; Non-ADD refers to cells taken from subjects diagnosed with non-Alzheimer's Disease dementia (e.g. Huntington's disease or Parkinsons's disease or Clinical Schizophrenia). The Alzheimer's Disease-specific molecular biomarkers in AD cells tested was a positive value falling between greater than about 0.02 and less than about 0.4. The Alzheimer's Disease-specific molecular biomarker in Mixed AD/PD/LBD clustered together at very low positive values, i.e. less than about 0.02 or about 0.03. The Alzheimer's Disease-specific molecular biomarkers in non-dementia age-matched control cells were negative or very low positive values, i.e. less than about 0.01. The Alzheimer's Disease-specific molecular biomarkers in non-ADD cells were negative values. Alzheimer's Disease-specific molecular biomarkers were measured by determining the ratio of phosphorylated Erk1 to phosphorylated Erk2 in cells that had been stimulated with bradykinin minus the ratio of phosphorylated Erk1 to phosphorylated Erk2 in cells that were stimulated with media lacking bradykinin. This is expressed as the following: Alzheimer's Disease-specific molecular biomarker={(pErk1/pErk2)$_{bradykinin}$}-{(pErk1/pErk2)$_{vehicle}$}. The ADSMB (noted as "Distinguishing Factor" (D.F.) in the figure) was plotted for four different categories of patients: Alzheimer's Disease (AD), mixed AD/PD/DLV (mixed diagnosis of Alzheimer's, Parkinson's and Lew body disease by autopsy confirmed) age matched control (AC) and non-AD dementia (Parkinson's disease and Huntington's disease) for Coriell cell repository and autopsy confirmed cell lines.

The present invention relates, in certain aspects, to methods of diagnosing Alzheimer's Disease in human cells taken from subjects that have been identified for testing and diagnosis. The diagnosis is based upon the discovery of unique Alzheimer's Disease-specific molecular biomarkers. In certain aspects, the invention is directed to methods of monitoring Alzheimer's Disease progression and to screening methods for the identification of lead compounds for treating or preventing Alzheimer's Disease. In certain aspects, the invention is directed to methods for determining or confirming the presence or absence of Alzheimer's Disease in a subject or in samples taken from a subject.

Because direct access to neurons in the brains of living human beings is impossible, early diagnosis of Alzheimer's Disease is extremely difficult. By measuring the Alzheimer's Disease-specific molecular biomarkers disclosed herein, the present invention provides highly practical, highly specific and highly selective tests for early diagnosis of Alzheimer's Disease. In addition, the Alzheimer's Disease-specific molecular biomarkers described herein provide a basis for following disease progression and for identifying therapeutic agents for drug development targeted to the treatment and prevention of Alzheimer's Disease.

The inventors have found a unique molecular biomarker for Alzheimer's Disease using peripheral (non-CNS) tissue that is useful in diagnostic assays that are highly sensitive and highly specific for the diagnosis of Alzheimer's Disease. A great advantage of the instant invention is that the tissue used in the assays and methods disclosed herein may be obtained from subjects using minimally invasive procedures, i.e., without the use of a spinal tap. Thus, one aspect of the invention is directed to an assay or test for the early detection of Alzheimer's Disease in a subject in which an internally controlled ratio of Erk1 phosphorylation to Erk2 phosphorylation, which is induced by a protein kinase C activator (such as bradykinin), is measured with specific antibodies using a baseline normalization response to growth media in human cells, such as skin fibroblasts, or other peripheral cells such as blood cells.

In the methods of the invention, the cells that are taken from the individual or patient can be any viable cells. Preferably, they are skin fibroblasts, but any other peripheral tissue cell (i.e. tissue cells outside of the central nervous system) may be used in the tests of this invention if such cells are more convenient to obtain or process. Other suitable cells include, but are not limited to, blood cells such as erythrocytes and lymphocytes, buccal mucosal cells, nerve cells such as olfactory neurons, cerebrospinal fluid, urine and any other peripheral cell type. In addition, the cells used for purposes of comparison do not necessarily have to be from healthy donors.

The cells may be fresh or may be cultured (see, U.S. Pat. No. 6,107,050, which is herein incorporated by reference in its entirety). In a specific embodiment, a punch skin biopsy can be used to obtain skin fibroblasts from a subject. These fibroblasts are analyzed directly using the techniques described herein or introduced into cell culture conditions. The resulting cultured fibroblasts are then analyzed as described in the examples and throughout the specification. Other steps may be required to prepare other types of cells which might be used for analysis such as buccal mucosal cells, nerve cells such as olfactory cells, blood cells such as erythrocytes and lymphocytes, etc. For example, blood cells can be easily obtained by drawing blood from peripheral veins. Cells can then be separated by standard procedures (e.g. using a cell sorter, centrifugation, etc.) and later analyzed.

Thus, the present invention relates, in certain aspects, to methods for the diagnosis and treatment of Alzheimer's Disease in a subject. In certain embodiments, the diagnostic methods of the invention are based on measuring the ratio of two specific and distinct phosphorylated MAP kinase proteins in cells taken from a subject which have been stimulated with an agent that is a protein kinase C activator. The invention is also directed, in certain embodiments, to kits containing reagents useful for the detection or diagnosis of Alzheimer's Disease. In certain aspects, the invention is directed to methods for screening to identify lead compounds useful for treating Alzheimer's Disease as well as to methods of using these compounds or chemical derivatives of the lead compounds in pharmaceutical formulations to treat or prevent Alzheimer's Disease in subjects in need thereof.

I. Definitions

As used herein, the term "sensitivity" in the context of medical screening and diagnosis, means the proportion of affected individuals who give a positive test result for the disease that the test is intended to reveal, i.e., true positive results divided by total true positive and false negative results, usually expressed as a percentage.

As used herein, the term "specificity" in the context of medical screening and diagnosis, means the proportion of individuals with negative test results for the disease that the test is intended to reveal, i.e., true negative results as a proportion of the total of true negative and false-positive results, usually expressed as a percentage.

As used herein, the term "highly sensitive" means a diagnostic method that is greater than or equal to about 50% sensitive, or about 55% sensitive, or about 60% sensitive, or about 65% sensitive, or about 70% sensitive, or about 75% sensitive, or about 80% sensitive, or about 85% sensitive, or about 90% sensitive, or about 95% sensitive, or about 96% sensitive, or about 97% sensitive, or about 98% sensitive, or about 99% sensitive or about 100% sensitive.

As used herein, the term "highly specific" means a diagnostic method that is greater than or equal to about 50% specific, or about 55% specific, or about 60% specific, or about 65% specific, or about 70% specific, or about 75% specific, or about 80% specific, or about 85% specific, or about 90% specific, or about 95% specific, or about 96% specific, or about 97% specific, or about 98% specific, or about 99% specific or about 100% specific.

As used herein, "lead compounds" are compounds identified using the methods of screening compounds disclosed herein. Lead compounds may have activity in shifting the Alzheimer's Disease-specific molecular biomarkers disclosed herein to values corresponding to those values calculated for Alzheimer's Disease-specific molecular biomarkers determined using normal healthy cells in the assays described herein. Lead compounds may be subsequently chemically modified to optimize or enhance their activity for use in pharmaceutical compositions for the treatment or prevention of Alzheimer's Disease.

As used herein, "sequence variants" are proteins that are related to each other both structurally and functionally. In certain embodiments, sequence variants are proteins that share structural similarity at the level of amino acid sequence and share functional attributes at the level of enzymatic activity. In certain embodiments, sequence variants are MAP kinase proteins that catalyze the phosphorylation of other proteins.

As used herein, the "absence of Alzheimer's Disease" means that a subject or cells taken from a subject do not exhibit a measurable or detectable Alzheimer's Disease phenotype.

As used herein, an "Alzheimer's Disease phenotype" in a subject or a cell sample includes but is not limited to an Alzheimer's Disease-specific molecular biomarker having a positive value greater than zero.

As used herein, an "Amyloid Beta Peptide" is any fragment of the Amyloid Beta Peptide or a full-length Amyloid Beta Peptide.

II. Methods of Diagnosing Alzheimer's Disease

The present invention is directed, in certain embodiments, to methods of diagnosing Alzheimer's Disease. In certain preferred embodiments, the diagnostic methods involve the steps of obtaining a cell sample from a subject, contacting the cell sample with an agent that is a protein kinase C activator and measuring the ratio of specific phosphorylated MAP kinase proteins in said cell sample to diagnose Alzheimer's Disease in said subject. In certain specific embodiments, the diagnostic assays disclosed herein may be carried out in vitro or in vivo. In a specific embodiment, the protein kinase C activator is bradykinin. In a further specific embodiment, the ratio of specific phosphorylated MAP kinase proteins is the ratio of phosphorylated Erk1 to phosphorylated Erk2, which is calculated by dividing the relative or normalized amount of phosphorylated Erk1 by the relative or normalized amount of phosphorylated Erk2.

Alzheimer's Disease-Specific Molecular Biomarkers

The diagnostic methods and methods of screening compounds useful for treating Alzheimer's Disease which are disclosed herein are based upon the discovery by the inventors of a unique molecular biomarker for Alzheimer's Disease. The numerical value of the Alzheimer's Disease-specific molecular biomarker will depend on certain variables, such as, for example, the cells used in the assay, the protein kinase C activator used in the assay and the specific MAP kinase proteins that are targeted for measurement of phosphorylation ratios.

In a specific embodiment, the Alzheimer's Disease-specific molecular biomarker may be measured by determining the ratio of phosphorylated Erk1 to phosphorylated Erk2 in cells that have been stimulated by a protein kinase C activator and subtracting from this the ratio of phosphorylated Erk1 to phosphorylated Erk2 in cells that have been stimulated with a control solution (vehicle) that lacks the protein kinase C activator. In certain embodiments, if the difference is greater than zero, i.e. a positive value, this is diagnostic of Alzheimer's Disease. In further preferred embodiments, if the difference is less than or equal to zero, this is indicative of the absence of Alzheimer's Disease.

In other embodiments, the Alzheimer's Disease-specific molecular biomarkers of the present invention are measured by determining the ratio of two phosphorylated MAP kinase proteins after stimulation of cells with a protein kinase C activator. The molecular biomarker may be measured by determining the ratio of a first phosphorylated MAP kinase protein to a phosphorylated second MAP kinase protein in cells that have been stimulated by a protein kinase C activator and subtracting from this the ratio of phosphorylated first MAP kinase protein to phosphorylated second MAP kinase protein in cells that have been stimulated with a control solution (vehicle) that lacks the protein kinase C activator. In certain preferred embodiments, if the difference is greater than zero, i.e. a positive value, this is diagnostic of Alzheimer's Disease. In further preferred embodiments, if the difference is less than or equal to zero, this is indicative of the absence of Alzheimer's Disease.

In certain embodiments, the Alzheimer's Disease-specific molecular biomarker is a positive numerical value in cell samples taken from patients diagnosed with Alzheimer's Disease (AD cells). In certain preferred embodiments, when the Alzheimer's Disease-specific molecular biomarker is measured by determining ratios of phosphorylated Erk1 to phosphorylated Erk2 in AD cells that have been stimulated with bradykinin, the positive numerical values for the Alzheimer's Disease-specific molecular biomarker in AD cells may range from about zero to about 0.5.

In certain embodiments, the Alzheimer's Disease-specific molecular biomarker is a negative numerical value when measured in cells taken from subjects diagnosed with non-Alzheimer's Disease dementia (non-ADD cells), such as, for example, Parkinson's disease or Huntington's disease or Clinical Schizophrenia. In certain preferred embodiments, when the Alzheimer's Disease-specific molecular biomarker is measured by determining ratios of phosphorylated Erk1 to phosphorylated Erk2 in non ADD cells that have been stimulated with bradykinin, the negative numerical values may range from about zero to about −0.2 or about −0.3.

In certain embodiments, the Alzheimer's Disease-specific molecular biomarker may be a negative numerical value, zero or very low positive numerical value in cell samples from age-matched control cells (AC cells) taken from patients who do not have Alzheimer's Disease. When the Alzheimer's Disease-specific molecular biomarker is measured by determining ratios of phosphorylated Erk1 to phosphorylated Erk2 in AC cells that have been stimulated with bradykinin, the Alzheimer's Disease-specific molecular biomarker in AC cells may range from less than about 0.05 to about −0.2.

In certain embodiments of the invention, the Alzheimer's Disease-specific molecular biomarkers may be measured by calculating the ratio of phosphorylated Erk1 to phosphorylated Erk2 in cells that have been stimulated with bradykinin minus the ratio of phosphorylated Erk1 to phosphorylated Erk2 in cells that have stimulated with a solution lacking bradykinin. This is expressed as the following: Alzheimer's Disease-specific molecular biomarker=$\{(pErk1/pErk2)_{bradykinin}\}-\{(pErk1/pErk2)_{vehicle}\}$.

Protein Kinase C Activators

Protein kinase C activators that are specifically contemplated for use in the diagnostic methods, kits and methods of screening to identify compounds of the instant invention include, but are not limited to: Bradykinin; α-APP modulator; Bryostatin 1; Bryostatin 2; DHI; 1,2-Dioctanoyl-sn-glycerol; FTT; Gnidimacrin, *Stellera chamaejasme* L; (−)-Indolactam V; Lipoxin $A_4$; Lyngbyatoxin A, *Micromonospora* sp.; Oleic acid; 1-Oleoyl-2-acetyl-sn-glycerol; 4 α-Phorbol; Phorbol-12,13-dibutyrate; Phorbol-12,13-didecanoate; 4α-Phorbol-12,13-didecanoate; Phorbol-12-myristate-13-acetate; L-α-Phosphatidylinositol-3,4-bisphosphate, Dipalmitoyl-, Pentaammonium Salt; L-α-Phosphatidylinositol-4,5-bisphosphate, Dipalmitoyl-, Pentaammonium Salt; L-α-Phosphatidylinositol-3,4,5-trisphosphate, Dipalmitoyl-, Heptaammonium Salt; 1-Stearoyl-2-arachidonoyl-sn-glycerol; Thymeleatoxin, *Thymelea hirsuta* L; insulin, phorbol esters, lysophosphatidylcholine, lipopolysaccharide, anthracycline dannorubicin and vanadyl sulfate. Also included are compounds known as "bryologues." Bryologues are described, for example, in Wender et al. Organic letters (United States) May 12, 2005, 7 (10) p 1995-8; Wender et al. Organic letters (United States) Mar. 17 2005, 7 (6) p 1177-80; Wender et al. Journal of Medicinal Chemistry (United States) Dec. 16 2004, 47 (26) p 6638-44. A protein kinase C activator may be used alone or in combination with any other protein kinase C activator in the diagnostic methods, kits and methods of screening compounds disclosed herein.

Bradykinin is a potent vasoactive nonapeptide that is generated in the course of various inflammatory conditions. Bradykinin binds to and activates specific cell membrane bradykinin receptor(s), thereby triggering a cascade of intracellular events leading to the phosphorylation of proteins known as "mitogen activated protein kinase" (MAPK). Phosphorylation of protein, the addition of a phosphate group to a Ser, Thr, or Tyr residue, is mediated by a large number of enzymes known collectively as protein kinases. Phosphorylation normally modifies the function of, and usually activates, a protein. Homeostasis requires that phosphorylation be a transient process, which is reversed by phosphatase enzymes that dephosphorylate the substrate. Any aberration in phosphorylation or dephosphorylation may disrupt biochemical pathways and cellular functions. Such disruptions may be the basis for certain brain diseases.

Measuring or Detecting Levels of Phosphorylated Proteins

The methods of diagnosing Alzheimer's Disease and methods of screening compounds to identify agents useful for the treatment or prevention of Alzheimer's Disease herein disclosed depend on measuring the Alzheimer's Disease-specific molecular biomarkers of the present invention.

In a preferred embodiment, the level of phosphorylated protein present in cells is detected by Western blotting. Protein levels of phosphorylated Erk1 or phosphorylated Erk2 can be measured in fibroblasts using anti-Erk1, anti-Erk2, anti-phospho-Erk1 and anti-phospho-Erk2 antibodies (Cell Signaling Technology). Levels of a different protein may also be measured in the same sample as a reference protein for normalization. Examples of possible reference proteins include, but are not limited to, annexin-II or actin.

In one embodiment, ELISA is performed according to the following procedures: 1) Add fibroblast cell lysates after treatment in duplicates or triplicates to a 96-well microplate that is previously coated with an anti-Erk antibody. 2) Incubate samples in microplate wells at room temperature for about 2 hours. 3) Aspirate samples and wash wells with a phosphate buffered saline (PBS)-based washing buffer. 4) Add working dilution of an anti-phospho-Erk1/2, or an anti-regular Erk1/2 antibody to each well, and incubate at room temperature for about 1 hour. 5) Aspirate and wash well with washing buffer. 6) Add a working dilution of a secondary antibody conjugated with horseradish peroxidase (HRP) to each well and incubate well at room temperature for about 30 min. 7) Aspirate and wash well with washing buffer. 8) Add stabilized Chromogen such as diaminobenzidine (DAB) and incubate at room temperature for about 30 min. 9) Add stop solution and measure the absorbance at 450 nm. Phosphorylation of Erk1/2 is assessed after normalization: $NR=A_P/A_R$. Where NR=the normalized ratio; $A_P$ is absorbance values for phospho-Erk1/2; and $A_R$ is absorbance for the total (regular) Erk1/2.

In a preferred embodiment, phosphorylation of Erk1/2 is assayed on Western blots using an anti-phospho-Erk1/2 antibody. Levels of the immunoreactive signals for phosphorylated Erk1/2 are quantified via densitometric scan. The mean density of the phospho-Erk1/2 signals are normalized with the mean density of total Erk1/2 signals that are detected from the same cell lysate samples with an anti-regular Erk1/2 antibody on a separate Western blot. The formula for normalization is: $NR=D_P/D_R$. Where NR (normalized ratio) represents Erk1/2 phosphorylation extent; $D_P$ is the mean density for phospho-Erk1/2, and $D_R$ is the mean density for the total amount of Erk1/2 detected on a Western blot from the same sample.

Immunoassays of the present invention for the detection of proteins may be immunofluorescent assays, radioimmunoassays, Western blot assays, enzyme immunoassay, immuno-precipitation, chemiluminescent assay, immunohistochemical assay, dot or slot blot assay and the like. (In "Principles and Practice of Immunoassay" (1991) Christopher P. Price and David J. Neoman (eds), Stockton Press, New York. N.Y., Ausubel et al. (eds) (1987) in "Current Protocols in Molecular Biology" John Wiley and Sons, New York, N.Y.). Detection may be by colorimetric or radioactive methods or any other conventional methods known to those having skill in the art. Standard techniques known in the art for ELISA are described in *Methods in Immunodiagnosis*, $2^{nd}$ Edition, Rose and Bigazzi, eds., John Wiley and Sons, New York 1980 and Campbell et al., *Methods of Immunology*, W.A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Pres, NY, N.Y.; Oellirich, M. 1984. *J. Clin. Chem. Clin. Biochem.* 22: 895-904 Ausubel, et al. (eds) 1987 in *Current Protocols in Molecular Biology*, John Wiley and Sons, New York, N.Y.

Cell Types, Protein Isolation and Antibodies

As stated previously, the cells taken from the patient being diagnosed may be any cell. Examples of cells that may be used include, but are not limited to, skin cells, skin fibroblasts, buccal mucosal cells, blood cells, such as erythrocytes, lymphocytes and lymphoblastoid cells, and nerve cells and any other cell expressing the Erk1/2 protein. Necropsy samples and pathology samples may also be used. Tissues comprising these cells may also be used, including brain tissue or brain cells. The cells may be fresh, cultured or frozen. Protein samples isolated from the cells or tissues may be used immediately in the diagnostic assay or methods for screening compounds or frozen for later use. In a preferred embodiment fibroblast cells are used. Fibroblast cells may be obtained by a skin punch biopsy.

Proteins may be isolated from the cells by conventional methods known to one of skill in the art. In a preferred method, cells isolated from a patient are washed and pelleted in phosphate buffered saline (PBS). Pellets are then washed with "homogenization buffer" comprising 50 nM NaF, 1 mM EDTA, 1 mM EGTA, 20 µg/ml leupeptin, 50 µg/ml pepstatin, 10 mM TRIS-HCl, pH=7.4, and pelleted by centrifugation. The supernatant is discarded, and "homogenization buffer" is added to the pellet followed by sonication of the pellet. The protein extract may be used fresh or stored at −80° C. for later analysis.

In the methods of the invention, the antibodies used in the disclosed immunoassays may be monoclonal or polyclonal in origin. The phosphorylated and non-phosphorylated Erk1/2 protein or portions thereof used to generate the antibodies may be from natural or recombinant sources or generated by chemical synthesis. Natural Erk1/2 proteins can be isolated from biological samples by conventional methods. Examples of biological samples that may be used to isolate the Erk1/2 protein include, but are not limited to, skin cells, such as, fibroblasts, fibroblast cell lines, such as Alzheimer's Disease fibroblast cell lines and control fibroblast cell lines which are commercially available through Coriell Cell Repositories, (Camden, N.J.) and listed in the National Institute of Aging 1991 Catalog of Cell Lines, National Institute of General Medical Sciences 1992/1993 Catalog of Cell Lines [(NIH Publication 92-2011 (1992)].

III. Kits for the Diagnosis of Alzheimer's Disease

It is further contemplated that this invention relates to kits which may be utilized in performing any of the diagnostic tests described above. The kits may contain a single diagnostic test or any combination of the tests described herein. The kits may comprise antibodies which recognize regular Erk1/2 (unphosphorylated Erk1 or unphosphorylated Erk2) or phosphorylated Erk1/2 (phosphorylated Erk1 or phosphorylated Erk2). The kits may contain antibodies that recognize regular MAP kinase proteins as well as phosphorylated MAP kinase proteins. The kits may also contain any one or more of the protein kinase C activators disclosed herein (such as, for example, bradykinin or bryostatin). Antibodies may be polyclonal or monoclonal. The kits may contain instruments, buffers and storage containers necessary to perform one or more biopsies, such as punch skin biopsies. The kits may also contain instructions relating to the determination of the ratios used to identify the Alzheimer's Disease-specific molecular biomarkers of the instant invention as well as the use of the antibodies or other constituents in the diagnostic tests. The instructions may also describe the procedures for performing a biopsy, such as a punch skin biopsy. The kits may also contain other reagents for carrying out the diagnostic tests such as antibodies for the detection of reference proteins used for normalization. Examples of antibodies that recognize possible reference proteins include, but are not limited to, antibodies that recognize annexin-II or actin. The kits may also include buffers, secondary antibodies, control cells, and the like.

IV. Methods of Screening Compounds Useful in the Treatment or Prevention of Alzheimer's Disease The present invention is also directed to methods to screen and identify substances useful for the treatment or prevention of Alzheimer's Disease. According to this embodiment, substances which reverse or improve the Alzheimer's Disease-specific molecular biomarkers described herein (i.e. back to levels found in normal cells) would be identified and selected as substances which are potentially useful for the treatment or prevention of Alzheimer's Disease.

By way of example, one such method of screening to identify therapeutic substances would involve the steps of contacting sample cells from an Alzheimer's Disease patient with a substance being screened in the presence of any of the protein kinase C activators disclosed herein and then measuring any of the Alzheimer's Disease-specific molecular biomarkers disclosed herein. An agent that reverses or improves the Alzheimer's Disease-specific molecular biomarker back to levels found in normal cells (i.e. cells taken from a subject without Alzheimer's Disease) would be identified and selected as a substance potentially useful for the treatment or prevention of Alzheimer's Disease.

In certain embodiments, an agent that reverses or improves an Alzheimer's Disease-specific molecular biomarker is an agent that causes a reduction of a positive value and/or a movement towards more negative values for an Alzheimer's Disease-specific molecular biomarker.

V. Methods of Monitoring the Progression of Alzheimer's Disease

Figure 2:
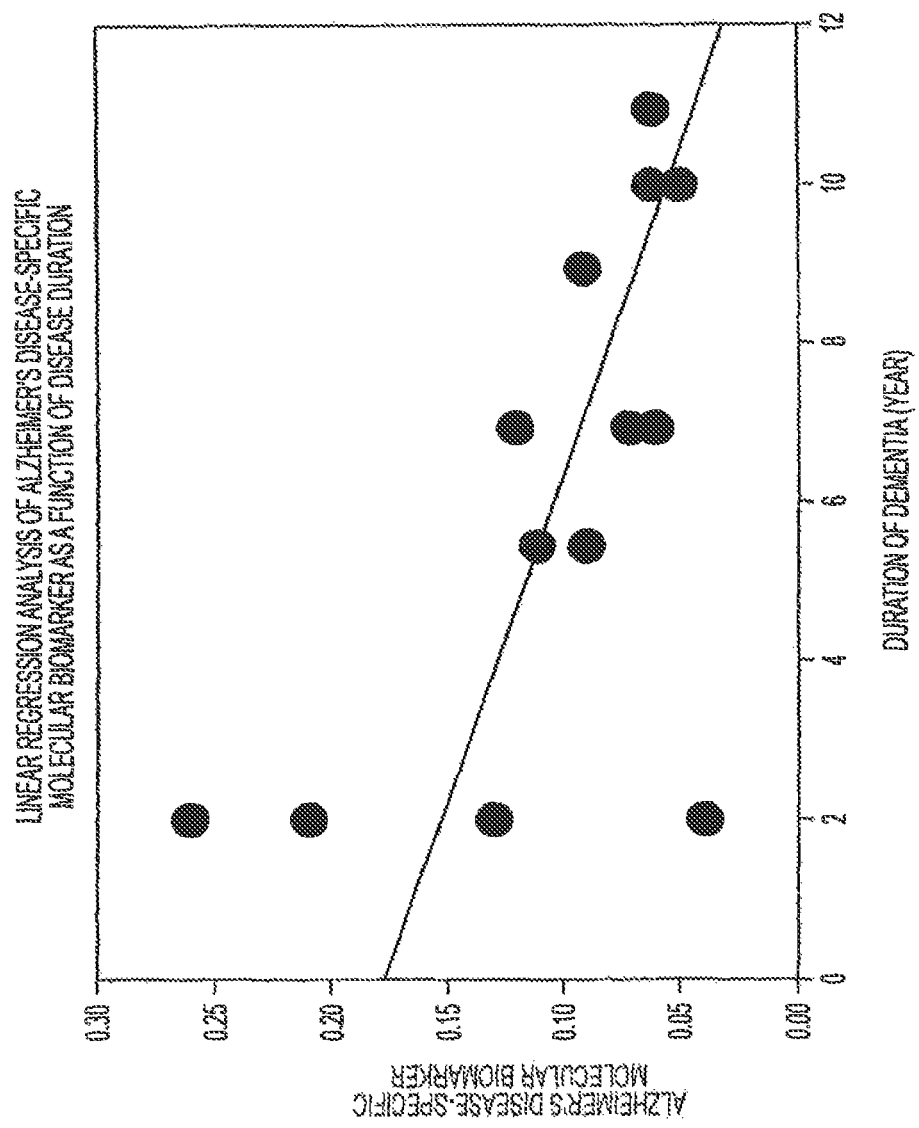
FIG. 2 shows a linear regression analysis of Alzheimer's Disease-specific molecular biomarkers as a function of years of dementia. The linear regression shows a negative slope of approximately −0.01 indicating an inverse correlation between years of dementia and positive magnitude of the Alzheimer's Disease-specific molecular biomarker. As the years of dementia increases (i.e. as Alzheimer's Disease progresses) the Alzheimer's Disease-specific molecular biomarker becomes a less positive numerical value. Measurement of the Alzheimer's Disease-specific molecular biomarker allows for early diagnosis of Alzheimer's Disease because a more highly positive value is indicative of early stages of the disease. Alzheimer's Disease-specific molecular biomarkers were measured by determining the ratio of phosphorylated Erk1 to phosphorylated Erk2 in cells that had been stimulated with bradykinin minus the ratio of phosphorylated Erk1 to phosphorylated Erk2 in cells that were stimulated with media lacking bradykinin. This is expressed as the following: Alzheimer's Disease-specific molecular biomarker=$\{(pErk1/pErk2)_{bradykinin}\}-\{(pErk1/pErk2)_{vehicle}\}$. Linear regression analysis of Alzheimer's Disease-specific molecular biomarker (ADSMB) as a function of disease duration of autopsy confirmed cases. Alzheimer's Disease-specific molecular biomarker is more effective in early years of the disease. This shows that the present method is more effective in early diagnosis of Alzheimer's Disease.

The present invention is also directed to methods of monitoring the progression of Alzheimer's Disease in a subject. FIG. 2 provides a linear regression analysis of Alzheimer's Disease-specific molecular biomarkers as a function of years of duration of dementia. The linear regression shows a negative slope of approximately −0.01 indicating an inverse correlation between years of dementia and positive magnitude of the Alzheimer's Disease-specific molecular biomarker. As the years of dementia increases (i.e. as Alzheimer's Disease progresses) the Alzheimer's Disease-specific molecular biomarker becomes a less positive numerical value. Measurement of the Alzheimer's Disease-specific molecular biomarker allows for early diagnosis of Alzheimer's Disease because, in certain embodiments, a more highly positive value is indicative of early stages of the disease. In certain embodiments, as Alzheimer's Disease progresses in a subject, the Alzheimer's Disease specific molecular biomarker becomes a less positive value.

Alzheimer's Disease-specific molecular biomarkers, in certain embodiments, are measured by determining the ratio of phosphorylated Erk1 to phosphorylated Erk2 in cells that have been stimulated with bradykinin minus the ratio of phosphorylated Erk1 to phosphorylated Erk2 in cells that have been stimulated with media lacking bradykinin. This is expressed as the following: Alzheimer's Disease-specific molecular biomarker=$\{(pErk1/pErk2)_{bradykinin}\}-\{(pErk1/pErk2)_{vehicle}\}$).

VI. Amyloid Beta Peptide

The terms "amyloid beta peptide", "beta amyloid protein", "beta amyloid peptide", "beta amyloid", "A. beta" and "A. beta peptide" are used interchangeably herein. In some forms, an amyloid beta peptide (e.g., A. beta 39, A. beta 40, A. beta 41, A. beta 42 and A. beta 43) is an about 4-kDa internal fragment of 39-43 amino acids of the larger transmembrane glycoprotein termed Amyloid Precursor Protein (APP). Multiple isoforms of APP exist, for example $APP^{695}$, $APP^{751}$, and $APP^{770}$. Examples of specific isotypes of APP which are currently known to exist in humans are the 695 amino acid polypeptide described by Kang et. al. (1987) Nature 325:733-736 which is designated as the "normal" APP; the 751 amino acid polypeptide described by Ponte et al. (1988) Nature 331:525-527 (1988) and Tanzi et al. (1988) Nature 331:528-530; and the 770-amino acid polypeptide described by Kitaguchi et al. (1988) Nature 331:530-532. As a result of proteolytic processing of APP by different secretase enzymes in vivo or in situ, A. beta is found in both a "short form", 40 amino acids in length, and a "long form", ranging from 42-43 amino acids in length. Part of the hydrophobic domain of APP is found at the carboxy end of A. beta, and may account for the ability of A. beta to aggregate, particularly in the case of the long form. A. beta. peptide can be found in, or purified from, the body fluids of humans and other mammals, e.g. cerebrospinal fluid, including both normal individuals and individuals suffering from amyloidogenic disorders.

The terms "amyloid beta peptide", "beta amyloid protein", "beta amyloid peptide", "beta amyloid", "A. beta" and "A. beta peptide" include peptides resulting from secretase cleavage of APP and synthetic peptides having the same or essentially the same sequence as the cleavage products. A. beta. peptides of the invention can be derived from a variety of sources, for example, tissues, cell lines, or body fluids (e.g. sera or cerebrospinal fluid). For example, an A. beta can be derived from APP-expressing cells such as Chinese hamster ovary (CHO) cells as described, for example, in Walsh et al., (2002), Nature, 416, pp 535-539. An A. beta. preparation can be derived from tissue sources using methods previously described (see, e.g., Johnson-Wood et al., (1997), Proc. Natl. Acad. Sci. USA 94:1550). Alternatively, A. beta. peptides can be synthesized using methods which are well known to those in the art. See, for example, Fields et al., Synthetic Peptides: A User's Guide, ed. Grant, W.H. Freeman & Co., New York, N.Y., 1992, p 77). Hence, peptides can be synthesized using the automated Merrifield techniques of solid phase synthesis with the a-amino group protected by either t-Boc or F-moc chemistry using side chain protected amino acids on, for example, an Applied Biosystems Peptide Synthesizer Model 430A or 431. Longer peptide antigens can be synthesized using well known recombinant DNA techniques. For example, a polynucleotide encoding the peptide or fusion peptide can be synthesized or molecularly cloned and inserted in a suitable expression vector for the transfection and heterologous expression by a suitable host cell. A. beta. peptide also refers to related A. beta sequences that results from mutations in the A. beta. region of the normal gene.

The A. beta-induced abnormality of the Erk 1/2 index (Alzheimer's Disease-specific molecular biomarker) may be used as a confirmatory test for either the presence or absence of Alzheimer's disease. Namely, a negative Amyloid Beta-Index response indicates the presence of disease, while a positive response indicates the absence of disease. That is, if an Alzheimer's Disease phenotype is induced in cells upon incubation or contact with an Amyloid Beta Peptide, this is indicative of the absence of the disease in the test cells or subject being tested. In contrast, if no or little change in an Alzheimer's Disease-specific molecular biomarker is induced in cells upon incubation or contact with an Amyloid Beta Peptide, this is indicative of the presence of Alzheimer's Disease in the test cells or subject being tested.

While amyloid beta (1-42) (i.e. Aβ (1-42)) is the preferred inducing stimulus, any other amyloid beta fragments such as (1-39), (1-40), (1-41), (1-43), (25-35), (16-22), (10-35), (10-35), (8-25), (28-38), (15-39), (15-40), (15-41), (15-42), (15-43) or any other amyloid beta fragment may also be used in any of the methods or kits described herein.

VII. Compositions Useful for the Treatment of Alzheimer's Disease

The present invention is also directed to compositions useful for the treatment or prevention of Alzheimer's Disease. Compounds identified using the screening methods described herein may be formulated as pharmaceutical compositions for administration to subjects in need thereof.

A pharmaceutical composition of the present invention or a compound (or a chemical derivative of a lead compound) identified using the screening methods disclosed herein can be administered safely by admixing with, for example, a pharmacologically acceptable carrier according to known methods to give a pharmaceutical composition, such as tablets (inclusive of sugar-coated tablets and film-coated tablets), powders, granules, capsules, (inclusive of soft capsules), liquids, injections, suppositories, sustained release agents and the like, for oral, subcutaneous, transdermal, transcutaneous or parenteral (e.g., topical, rectal or intravenous) administration.

Examples of pharmacologically acceptable carriers for use in the pharmaceutical compositions of the invention include, but are not limited to various conventional organic or inorganic carriers, including excipients, lubricants, binders and disintegrators for solid preparations, and solvents, solubilizers, suspending agents, isotonic agents, buffers, soothing agents, and the like for liquid preparations. Where necessary, conventional additives such as antiseptics, antioxidants, coloring agents, sweeteners, absorbents, moistening agents and the like can be used appropriately in suitable amounts.

Examples of excipients for use in the pharmaceutical compositions of the invention include, but are not limited to agents such as lactose, sucrose, D-mannitol, starch, corn starch, crystalline cellulose, light anhydrous silicic acid, polysaccharides, disaccharides, carbohydrates, trehalose and the like.

Examples of lubricants for use in the pharmaceutical compositions of the invention include, but are not limited to agents such as magnesium stearate, calcium stearate, talc, colloidal silica and the like.

Examples of binders for use in the pharmaceutical compositions of the invention include, but are not limited to crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of disintegrators for use in the pharmaceutical compositions of the invention include, but are not limited to starch, carboxymethylcellulose, carboxymethylcellulose calcium, sodium carboxymethyl starch, L-hydroxypropylcellulose and the like.

Examples of solvents for use in the pharmaceutical compositions of the invention include, but are not limited to water for injection, alcohol, propylene glycol, Macrogol, sesame oil, corn oil, olive oil and the like.

Examples of solubilizers for use in the pharmaceutical compositions of the invention include, but are not limited to polyethylene glycol, propylene glycol, D-mannitol, benzyl benzoate, ethanol, tris-aminomethane, cholesterol, triethanolamine, sodium carbonate, sodium citrate and the like.

Examples of suspending agents for use in the pharmaceutical compositions of the invention include, but are not limited to surfactants such as stearyl triethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of isotonic agents for use in the pharmaceutical compositions of the invention include, but are not limited to glucose, D-sorbitol, sodium chloride, glycerine, D-mannitol and the like.

Examples of buffers for use in the pharmaceutical compositions of the invention include, but are not limited to phosphate, acetate, carbonate, citrate etc., and the like.

Examples of soothing agents for use in the pharmaceutical compositions of the invention include, but are not limited to benzyl alcohol and the like.

Examples of antiseptics for use in the pharmaceutical compositions of the invention include, but are not limited to p-oxybenzoates, chlorobutanol, benzyl alcohol, phenethyl alcohol, dehydroacetic acid, sorbic acid and the like.

Examples of antioxidants for use in the pharmaceutical compositions of the invention include, but are not limited to sulfite, ascorbic acid, α-tocopherol and the like.

In certain embodiments when the pharmaceutical composition of the present invention is used as an injection, a carrier for injection to be used may include any or all of the following: a solvent, a solubilizer, a suspending agent, an isotonic agent, a buffer, a soothing agent and the like. Examples of the solvent include, but are not limited to water for injection, physiological saline, Ringer's solution and the like. Examples of the solubilizer include, but are not limited to polyethylene glycol, propylene glycol, D-mannitol, benzyl benzoate, trisaminomethane, cholesterol, triethanolamine, sodium carbonate, sodium citrate and the like. Examples of the isotonic agent include but are not limited to glucose, D-sorbitol, sodium chloride, glycerin, D-mannitol and the like. Examples of the buffer include but are not limited to buffers such as phosphate, acetate, carbonate, citrate and the like, and the like. Examples of the soothing agent include but are not limited to benzyl alcohol and the like. Examples of the pH adjusting agent include but are not limited to hydrochloric acid, phosphoric acid, citric acid, sodium hydroxide, sodium bicarbonate, sodium carbonate and the like.

In certain embodiments, the composition for injection of the present invention may be freeze-dried in an aseptically treated freeze dryer and preserved in a powder state, or can be sealed in a container for injection (e.g., ampoule) and preserved.

In addition, the pharmaceutical composition of the present invention may be diluted with the aforementioned carrier for injection when in use.

The content of an active compound in the pharmaceutical composition of the present invention may vary depending on the form of the preparation, but it is generally about 0.01-about 99 wt %, preferably about 0.1-about 50 wt %, more preferably about 0.5-about 20 wt %, of the whole preparation.

The content of nonionic surfactant in the pharmaceutical composition of the present invention may vary depending on the form of the preparation, but it is generally about 1 to about 99.99 wt %, preferably about 10 to about 90 wt %, more preferably about 10 to about 70 wt %, of the whole preparation.

The content of ethanol, benzyl alcohol or dimethylacetamide in the pharmaceutical compositions of the present invention may vary depending on the form of the preparation, but it is generally about 1 to about 99.99 wt %, preferably about 10 to about 90 wt %, more preferably about 30 to about 90 wt %, of the whole preparation.

The mixing ratio (weight ratio) of nonionic surfactant and ethanol in the pharmaceutical compositions of the present invention is not particularly limited, and is, for example, nonionic surfactant:ethanol=about 0.01-99.99:99.99-0.01, preferably about 1-99:99-1, more preferably about 10-90:90-10 and the like. More preferably, nonionic surfactant:ethanol=about 10-80:90-20, about 50-80:50-20 and the like, and particularly, about 20:80, about 65:35 and the like are preferable.

The content of cyclodextrin derivative readily soluble in water in the pharmaceutical composition of the present invention varies depending on the form of the preparation, but it is generally about 1 to about 99.99 wt %, preferably about 10 to about 99.99 wt %, more preferably about 20 to about 97 wt %, particularly preferably about 50 to about 97 wt %, of the whole preparation.

The content of other additives in the pharmaceutical composition of the present invention may vary depending on the form of the preparation, but it is generally about 1 to about 99.99 wt %, preferably about 10 to about 90 wt %, more preferably about 10 to about 70 wt %, of the whole preparation.

The pharmaceutical compositions of the present invention may be a pharmaceutical composition comprising an active compound, a nonionic surfactant and a cyclodextrin derivative readily soluble in water. In this case, the content of each component, i.e. the active compound, the nonionic surfactant and the cyclodextrin derivative readily soluble in water is the same as in the aforementioned ranges.

VIII. Methods of Treating Alzheimer's Disease

The present invention is also directed to methods of treating or preventing Alzheimer's Disease using the pharmaceutical compositions disclosed herein.

The compounds of the present invention may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The pharmaceutical compositions and method of the present invention may further comprise other therapeutically active compounds which are usually applied in the treatment of Alzheimer's Disease.

In the treatment or prevention of Alzheimer's Disease an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be about 0.005 to about 0.05, 0.05 to 0.5 or 0.5 to 5 mg/kg per day. For oral administration, the compositions are preferably provided in the form of tablets containing about 1 to 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

All of the references, patents and printed publications mentioned in the instant disclosure are hereby incorporated by reference in their entirety into this application.

The following examples are provided by way of illustration to further describe certain preferred embodiments of the invention, and are not intended to be limiting of the present invention.

EXAMPLES

Example 1: Alzheimer's Disease-Specific Molecular Biomarker (ADSMB)

Figure 3:
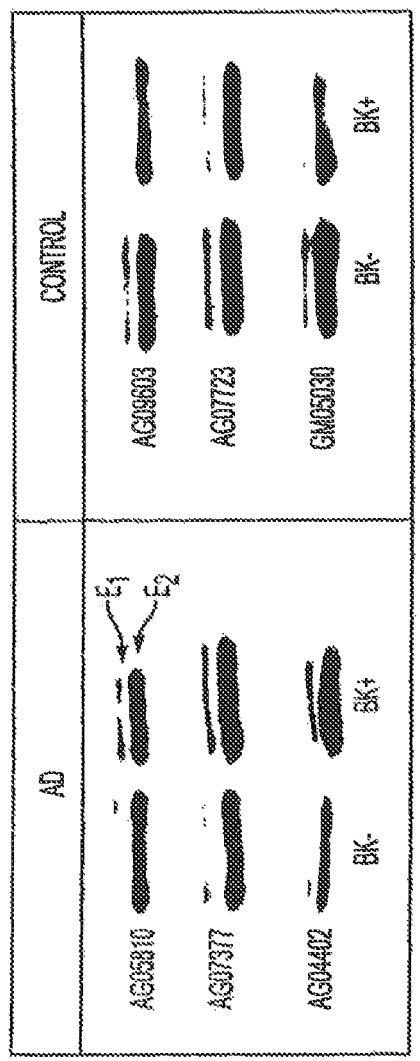
FIG. 3 shows western blot data of p-Erk1/2 (phosphorylated Erk1 and Erk2) after bradykinin (BK+) treatment and vehicle (DMSO, without bradykinin, BK−) for AD and control cell lines. For bradykinin treatment (BK+), serum free (24 hrs) cells were treated with 10 nM bradykinin for 10 min at 37° C. The corresponding vehicle treatment (BK−), serum free (24 hrs) cells were treated with the same amount of DMSO (without BK) for 10 min at 37° C. After 10 min P-Erk1/2 bands were darker for BK+ than that of BK− treatment for AD cell line, but it is reverse for control cell lines. This shows that BK induced activation of Erk was higher for AD cell lines.
Figure 4B:
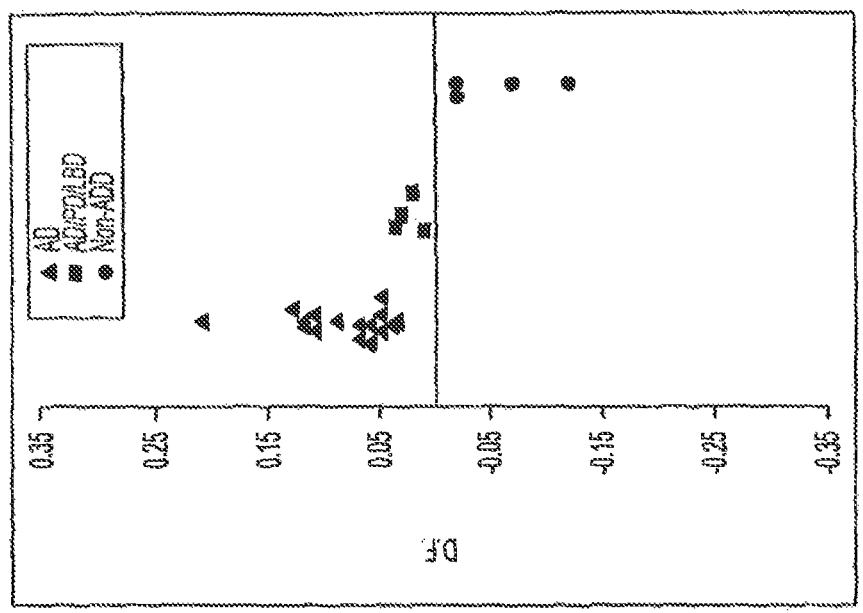
FIGS. 4A and 4B show Alzheimer's Disease-Specific Molecular Biomarker (ADSMB) (noted as the "Distinguishing Factor" (D.F.) in the figure) calculated as discussed herein. ADSMB was plotted for AD (Alzheimer's Disease), AC (age matched control) and non-ADD (non AD dementia, e.g. Parkinson's disease Lewy body disease) cell lines from Coriell repository (A) (Coriell Institute of Medical Research, Camden, N.J.) and cell lines provided by Neurologic Inc. (autopsy confirmed) (B). The results show that ADSMB for AD cases was consistently higher than for AC and non-ADD cases.
Figure 4A:
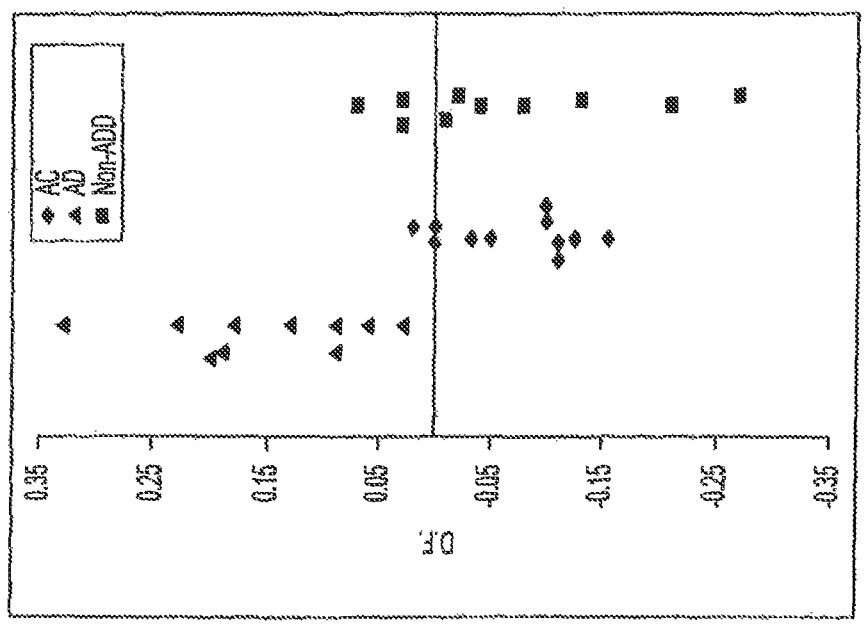
Figures 6A, 6B:
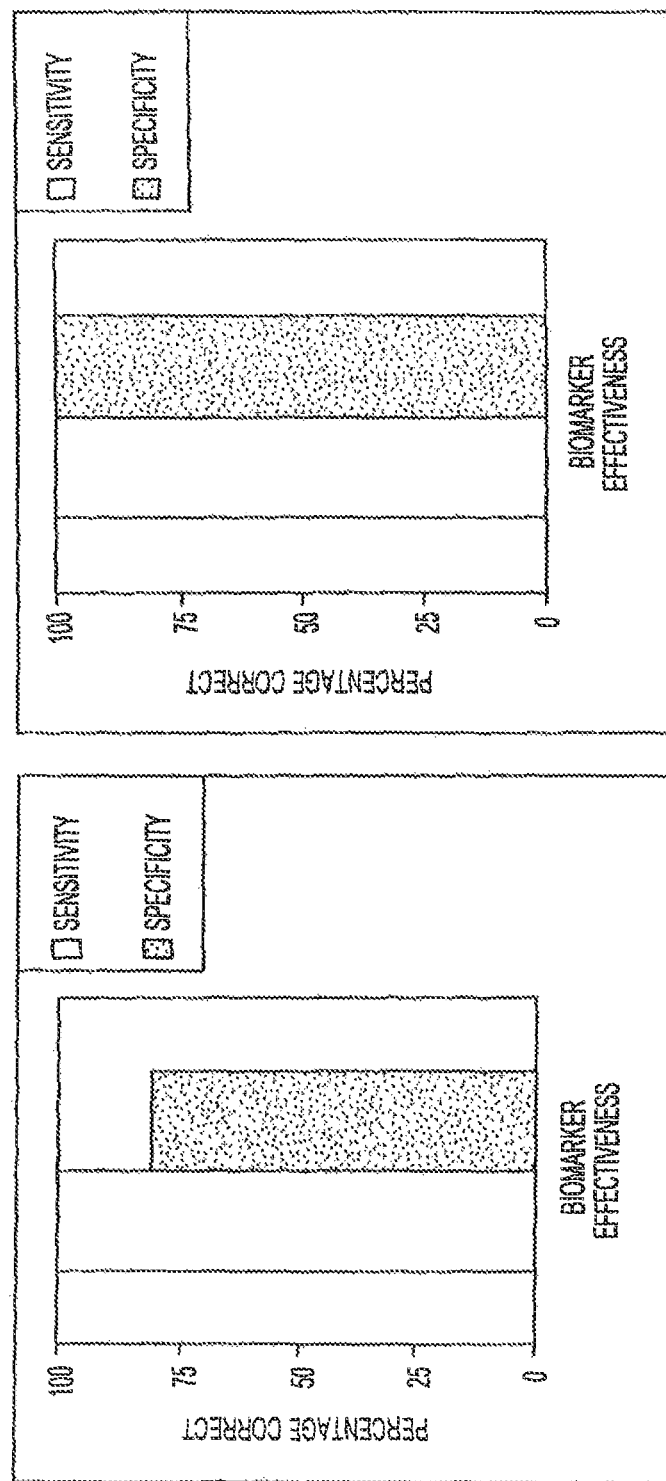
FIGS. 6A and 6B shows a decision matrix analysis of the ADSMB. Sensitivity and specificity of the biomarker are plotted to show the effectiveness to detect the disease for Coriell cell repository (A) and autopsy confirmed (B) cells.

Bradykinin (10 nM, 10 min at 37° C.) was found to cause greater phosphorylation of Erk1/2 in Alzheimer's (AD) fibroblasts vs. non-AD dementia and non-demented control fibroblasts. While this increased Erk1/2 phosphorylation for AD fibroblasts could be observed here with additional Coriell Cell lines, the inherent variability found in these measurements indicated a need for improved quantitation, reliability, and reproducibility. Here, therefore, to control for intrinsic differences in growth rates of the fibroblast cell lines, as well as differences in the exact quantities of protein extracts applied to the gels, we introduce a new measure of phosphorylation—one that compares Erk1 to Erk2 phosphorylation in every patient sample using a Erk1/2 ratio before and after BK+ stimulation. This measure of Erk1/Erk2 phosphorylation ratio, the Alzheimer's Disease-Specific Molecular Biomarker (ADSMB), completely distinguished all non-demented control fibroblasts from all AD fibroblasts (FIGS. 1 and 4A). The apparent higher level of p-Erk1 for control cases (BK−) (FIG. 3) was not consistent for all patients. A few cases of non-AD dementia were not distinguished, although these can be due to the lack of autopsy confirmation of the clinical diagnoses. This interpretation was supported by the results of the ADSMB measurement obtained with fibroblasts from patients with autopsy-confirmed diagnoses (FIGS. 1 and 4B), in which the ADSMB accurately distinguished all AD cases from all non-AD dementias and even cases of "mixed" dementia due to both AD and other non-AD etiologies such as Parkinson's disease. This high accuracy in distinguishing AD from both non-AD dementia and non-demented control patients is reflected in the remarkable sensitivity and specificity of the ADSMB (FIG. 6) considering both the Coriell cell samples and the autopsy-confirmed samples. When only the autopsy-confirmed diagnoses are considered, sensitivity and specificity are at the 100% levels.

Alzheimer's Disease-Specific Molecular Biomarker (ADSMB) Varies with Disease Duration For a sample of those patients for whom disease duration was available (i.e. time of ADSMB measurement from the time of symptom(s) onset), we examined the relation of ADSMB amplitudes to disease duration. As illustrated (FIG. 2), there was a significant (with linear regression analysis) inverse correlation of ADSMB magnitude with disease duration. These results suggest that the MAP Kinase phosphorylation ADSMB is more marked, the earlier time in the course of the disease at which it is measured.

Induction of Alzheimer's Phenotype by Aβ (1-42)

Figure 5A:
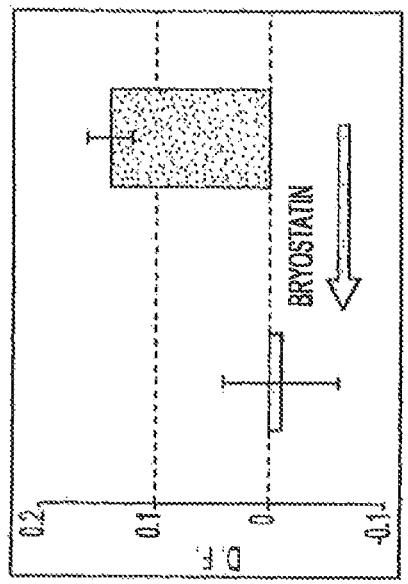
FIGS. 5A and 5B show soluble Aβ induces and bryostatin treatment reverses Alzheimer's phenotype of human fibroblast. (A) Alzheimer's Disease-Specific Molecular Biomarker (noted as "Distinguishing Factor" (D.F.) in the figure) was measured for control (non-AD) cell lines (AG07723, AG11363, AG09977, AG09555 and AG09878) as described herein and found small and negative. After 1.0 μM Aβ-42 treatment (ADSMB) was measured again as described and found higher and positive. This shows that the bradykinin induced, activated Erk1/Erk2 ratio becomes higher after 1.0 μM Aβ(1-42) treatment. AC cell lines behave like AD phenotype after Aβ(1-42) treatment. (B) ADSMB ("Distinguishing Factor" (D.F.)) was measured after 1.0 μM Aβ(1-42) treatment for 24 hrs for AC cell lines. The ADSMB values were higher and positive as found earlier. The same cell lines were treated first with 1.0 μM Aβ(1-42) for 24 hrs and followed by 0.1 nM bryostatin treatment for 20 min. The ADSMB (D.F.) values were again measured and found small and negative. This shows that soluble Aβ-induced changes can be reversed by bryostatin therapy.

Because Aβ(1-42) levels are most likely to be critically involved in early AD, and because the observed ADSMB was shown by the data to have early AD diagnostic power, we examined here the possibility that elevated Aβ(1-42) might induce abnormalities of MAP kinase D.F. Fibroblast cell lines from normal control patients, therefore, were exposed for 24 hours to 1.0 μM Aβ(1-42). As illustrated in FIG. 5A, preincubation with Aβ(1-42) did, as predicted, convert the normal (negative) ADSMB phenotype into the abnormal positively valued ADSMB phenotype that had been observed for all of the AD phenotypes. These results suggest that this ADSMB phenotype in AD patients actually arose from elevated levels of Aβ(1-42).

Reversal of Alzheimer's Phenotype by the PKC Activator, Bryostatin

Figure 5B:
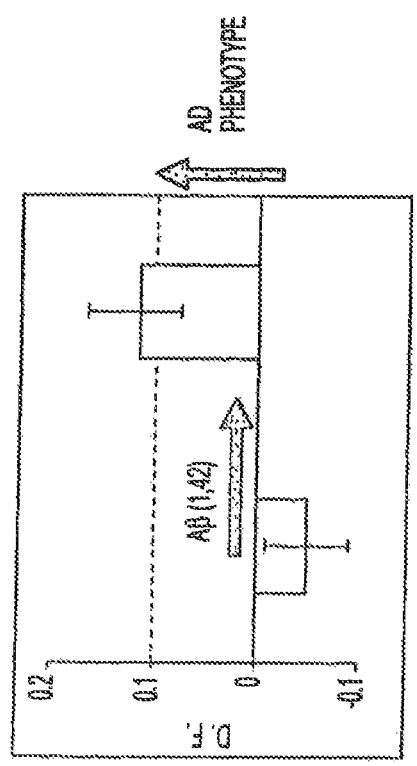

As discussed earlier, MAP Kinase phosphorylation (measured by the ADSMB) is regulated by PKC activation that, in turn showed vulnerability to elevated levels of Aβ. Furthermore, the potent PKC activator, the macrolactone, Bryostatin, was found to enhance PKC activation in human fibroblasts as well as to reduce Aβ(1-42) levels in the brains of transgenic mice with human AD genes. Based on these findings, therefore, we tested the effects of Bryostatin (0.1 nM) on Aβ(1-42)—treated human fibroblasts. As illustrated (FIG. 5B and Table 1), Bryostatin entirely reversed the change of MAP Kinase phosphorylation induced in normal fibroblasts by Aβ(1-42). Bryostatin changed the abnormal, positively valued of Aβ-treated fibroblasts into the normal, negatively valued ADSMB previously observed for non-AD fibroblasts. This "therapeutic" efficacy of Bryostatin is consistent with the greatly increased survival of AD-transgenic mice that were exposed to chronic

TABLE 1

Alzheimer's Disease-Specific Molecular Biomarker (ADSMB) was measured for AC (control cell lines) (control), amyloid beta (Aβ) induced cells and, amyloid beta (Aβ) induced cells plus bryostatin treatment (Aβ + BY).

| Cell lines | ADSMB[a] | | |
|---|---|---|---|
| | Control* | Aβ*[#] | Aβ + BY[#] |
| AG06959 | — | 0.13 | 0.0 |
| AG07732 | −0.11 | 0.12 | −0.13 |
| AG11363 | 0.0 | 0.16 | 0.09 |
| AG09977 | −0.15 | 0.13 | 0.01 |
| Average ± SE | −0.09 ± 0.05 | 0.13 ± 0.01 | −0.01 ± 0.05 |

*$P < 0.001$,
[#]$P < 0.01$
[a]ADSMB was calculated according to method use by this study.
*T-test was conducted between control and Aβ treated cells.
[#]T-test was conducted between Aβ treated cells and Aβ plus bryostatin treated cells.

The high sensitivity and specificity of the ADSMB measure of MAP Kinase phosphorylation to diagnose AD suggest an important potential as a laboratory test for AD to aid in the clinical assessment of dementia. To date, autopsy confirmation of clinically-diagnosed dementia is usually available only for patients with long-standing disease. Considering that AD can last for 8-15 years, clinical diagnosis for AD of brief duration has been found to show high inaccuracy when it is compared to clinical diagnosis later in the disease progression and then subjected to autopsy validation. Thus a peripheral biomarker, here a MAP kinase phosphorylation ratio for human fibroblasts, has real utility in arriving at therapeutic strategies for dementia.

Although not wishing to be bound by theory, it is also of interest to consider why the ratio of Erk1 to Erk2 phosphorylation might be sensitive to abnormalities due to AD-specific differences of Aβ metabolism. One implication of this and past studies of peripheral biomarkers for AD is that the pathophysiology of AD does not only involve the brain, but also a variety of other organ systems. This systemic pathophysiologic view of AD is consistent with observations that amyloid and tan metabolic pathways are ubiquitous in the human body and manifest in blood, saliva, skin and extra-brain tissues.

The close correlation shown here of the Erk1/Erk2 ratio with AD also focuses attention on these substrates as a "read-out" of AD signaling. For example, PKC isozymes regulate several molecular targets that converge on MAP Kinase. PKC activates: (1) α-secretase increase of s-APP and, thus, indirectly, reduction of β-amyloid; (2) β-amyloid activates glycogen synthase Kinase-3β (GSK-3β) that increases MAP kinase Phosphorylation; (3) PKC inhibits GSK-3β; (4) PKC itself phosphorylates GSK-33; and (5) PKC activates cytokines inflammatory signals that may respond to BK and other AD-initiated events; (6) Toxic cholesterol metabolites (e.g. 17-OH cholesterol) inhibit PKC α that, on balance reduces Aβ, and reduces phosphorylated tau.

Evidence that dysfunction of PKC isozymes themselves may contribute to the earliest initiation of the AD process, therefore, reflected, via all of the above signaling events, in abnormality of the Erk1/2 phosphorylation ratio.

Finally, it is also a mystery as to how the specificity of AD phosphorylation abnormality may be maintained through the successive passages of human fibroblast cell lines. This phenomenon might be accounted for through an interaction of PKC/MAP kinase levels with the fibroblast genome. It is known that PKC and MAP kinase regulate gene expression. It may be possible, therefore, that an ongoing cycle of PKC/MAP Kinase stimulation of their own synthesis could perpetuate the abnormalities of PKC levels and MAP Kinase phosphorylation from one generation of human fibroblasts to the next.

Example 2: Aβ Treatment

Preparation of Aβ(1-42) solution: Initially 1 mg of Aβ(1-42) was dissolved in hexa-fluoroisopropanol (Sigma, St. Louis, Mo.) at a concentration of 3 mM and separated into aliquots in sterile microcentrifuge tubes. Hexa-fluoroisopropanol was removed under vacuum and lyophilized. The Aβ(1-42) films were stored at −20° C. under dry conditions until use. 5 mM Aβ(1-42) stock solution was prepared from the stored Aβ(1-42) in DMSO just before the experiment. 1.0 μM stock solution was prepared in DMEM medium (supplemented with 10% serum and penicillin/streptomycin) by dissolving Aβ(1-42) from a DSMO stock solution. DMEM medium containing 1.0 μM Aβ(1-42) was added to non-AD control (AC) cells at 90-100% confluence stage in 25 mL cultured flask and kept at cell culture incubator (at 37° C. with 5% $CO_2$) for 24 hrs. Cells were 'starved' in serum free medium (DMEM) for 16 hours. 10 nM bradykinin (in DMSO) solution was prepared in DMEM medium with 10% serum. 7 mL of 10 nM BK solution were added to the 25 mL cultured flask and incubated at 37° C. for 10 min. For the controls, the same amount of DMSO was added in DMEM medium with 10% serum. 7 mL of this medium with DMSO (<0.01%) were added to the 25 mL cultured flask and incubated at 37° C. for 10 min. After washing four times with cold (4° C.) 1×PBS, flasks were kept in a dry ice/ethanol mixture for 15 min. Flasks were removed from the dry ice/ethanol mixture and then 100 μL of lysis buffer (10 mM Tris, pH 7.4, 150 mM NaCl, 1 mM EDTA, 1 mM EGTA, 0.5% NP-40, 1% Triton X-100, 1% protease inhibitor cocktail, 1% ser/thr/tyrosine phosphatase inhibitor cocktails) was added into each flask. Flasks were kept on an end-to end shaker in a cold room (4° C.) for 30 min and cells were collected from each flask with a cell scraper. Cells were sonicated and then centrifuged at 14000 rpm for 15 min, and the supernatant was used for Western blotting after total protein assay. Total Erk1, Erk2 and the phosphorylated forms of Erk1 and Erk2 (p-Erk1, p-Erk2) were determined using specific antibodies: anti-regular Erk1/2 and anti-phospho ERK1/2. At least three bradykinin treated flasks (BK+)

and correspondingly three control flasks (BK−) were included for each cell line to minimize errors in measurement.

Bryostatin Treatment 0.1 nM bryostatin solution was prepared in regular DMEM medium (supplemented with 10% serum and penicillin/streptomycin) from DMSO stock solution. After Aβ treatment, cells were washed four times with regular culture medium (supplemented with 10% serum and penicillin/streptomycin). 0.1 nM bryostatin was added to cells and culture flasks were kept in the cell culture incubator (at 37° C. with 5% $CO_2$) for 20 min. After five times washing with serum free medium the flasks were kept in an incubator (at 37° C. with 5% $CO_2$) in serum free condition for 16 hrs. The Bradykinin induced MAPK assay was done as discussed above.

Data Analysis

Signals of the Western blot protein bands were scanned with a Fuji LAS-1000 Plus scanner. The intensity of Erk1, Erk2, p-Erk1 and p-Erk2 were measured from scanned protein bands by a specially designed software developed by Dr. Nelson in our Institute (Blanchette Rockefeller Neurosciences Institute, Rockville, Md.). The intensity was measured by strip densitometry. The protein bands were selected by strip and each pixel density was calculated after background subtraction by the software. The ratios of p-Erk1/p-Erk2 were calculated from sample (BK+) and control (BK−) respectively. The following formula was used to distinguish between AD and non-AD cases:

$$ADSMB=[\text{p-Erk1/p-Erk2}]^{BK+}-[\text{p-Erk1/p-Erk2}]^{BK-}$$

ADSMB=Alzheimer's Disease-Specific Molecular Biomarker

Example 3: In Vitro Assay of Skin Fibroblasts to Determine Ratio of Phosphorylated Erk1 to Phosphorylated Erk2

Banked skin fibroblasts cells (Alzheimer's Disease (AD), non AD dementia (non-ADD) (e.g. Huntington and Parkinson disease and Clinical Schizophrenia) and age-matched control cells (AC), from Coriell Institute of Medical Research were cultured to 90-100% confluence stage. Cells were "starved" in serum-free medium (DMEM) for 16 hours. 10 nM of Bradykinin (BK) in DMSO in regular medium was added at 37° C. for 0 and 10 min. For the controls, the same amount of DMSO was added.

After washing four times with cold (4° C.) 1×PBS, flasks were kept in dry ice/ethanol mixture for 15 min. Flasks were removed from dry ice/ethanol mixture and then 80 μL of lysis buffer (10 mM Tris, pH 7.4, 150 mM NaCl, 1 mM EDTA, 1 mM EGTA, 0.5% NP-40, 1% Triton X-100, 1% protease inhibitor cocktail, 1% ser/thr/tyrosine phosphatase inhibitor cocktails) was added into each flask.

Flasks were kept on an end-to-end shaker in a cold room (4° C.) for 30 min and cells were collected from each flask with a cell scraper. Cells were sonicated and then centrifuged at 14000 rpm for 15 min, and the supernatant was used for Western blotting after total protein assay.

Total Erk1, Erk2 and the phosphorylated forms of Erk1 and Erk2 (p-Erk1, p-Erk2) were determined using specific antibodies: anti-regular Erk1/2 and anti-phospho ERK1/2.

Example 4: Skin Fibroblasts

Banked skin fibroblasts from patients with AD and age-matched controls are purchased from the Coriell Institute for Medical Research. Autopsy confirmed skin fibroblasts are obtained separately. Patients may be clinically affected with severe dementia, progressive memory loss, and other impaired cognitive functions. Brains from these patients show abnormal BEG and different degrees of cerebral atrophy by CAT or CT scan. Cells from normal individuals with close age matches are used as controls.

Fresh-taken skin fibroblasts. The collection and culture of fibroblasts from freshly obtained skin tissue is performed as follows: Punch-biopsy skin tissues from non-FAD (nFAD) patients and age-matched controls are obtained by qualified personnel. All patients (or representatives) sign informed consent forms.

Banked fibroblasts from Huntington's disease. These fibroblasts are from Huntington's disease (HD) patients, with dementia accompanying typical Huntington's disease symptoms. Fibroblasts from normal age- and gender-matched individuals are used as controls.

Example 5: Materials

DMEM is purchased from Gibco BRL. Fetal bovine serum is purchased from Bio Fluids. Bradykinin, diphenylboric acid 2-aminoethyl ester (2ABP), protease, and phosphatase inhibitor cocktails are purchased from Sigma; bisindolylmaleimide-1 and LY294002 are purchased from Alexis; PD98059 is purchased from Cell Signaling Technology. Anti-phospho-Erk1/2 antibodies are purchased from Cell Signaling Technology. Anti-regular Erk1/2 is purchased from Upstate Biotechnology. SDS minigels (4-20%) are purchased from Invertrogene-Novex. Nitrocellulose membranes are purchased form Schleicher & Schuell (Keene, N.H.). All the SDS electrophoresis reagents are purchased from Bio-Rad. The SuperSignal chemilumines-cence substrate kit is purchased from Pierce.

Alternatively, Bradykinin (M.Wt. 1060.2) was purchased from Calbiochem (San Diego, Calif.). Anti phospho-p44/p42 MAPK from rabbit was obtained from Cell Signaling Technology (Danvers, Mass.). Anti-regular Erk1/2 was purchased from Upstate Biotechnology, (Charlottesville, Va.), Anti-rabbit secondary antibody was purchased from Jackson Lab (Bar Harbor, Me.). Beta amyloid (1-42) (M.Wt. 4514.1) was procured from American Peptide (Sunnyvale, Calif.). Bryostatin was purchased from Biomol (Plymouth Meeting, Pa.).

Example 6: Culture of AC and AD Fibroblast Cells

Banked fibroblasts from Alzheimer's Disease patients including both FAD and nFAD types, and from age-matched controls (AC), are maintained and cultured in T25/T75 flasks with DMEM containing 10% fetal bovine serum (FBS). Cells are used within passages 6 to 17.

Example 7: Processing and Culture of Fibroblasts from Fresh Biopsy Tissue or Banked Samples Samples are placed in 1×PBS and transported in transfer medium to the laboratory for propagation. After the transfer medium is removed, the skin tissues are rinsed with PBS and finely chopped into 1-mm-sized explants. The explants are transferred one by one onto the growth surface of vented T25 flasks with 3 ml of biopsy medium containing 45% PBS and 100 U/ml penicillin and 100 U/ml streptomycin (Pen/Strep). The tissues are cultured at 37 C. for 24 h before addition of 2 ml of biopsy medium containing 10% FBS. The medium is replaced after 48 h with 5 ml of regular culture medium containing 10% FBS and 100 U/ml Pen/Strep. The cells are then passaged and maintained according to a regular procedure given above.

Human skin fibroblast cell culture systems have also been used for these studies. Banked skin fibroblasts cells Alzheimer's Disease (AD), non AD dementia (e.g. Huntington and Parkinson disease and Clinical Schizophrenia and age-matched control, AC) from Coriell Institute of Medical Research (Camden, N.J.) were cultured (supplemented with 10% serum and penicillin/streptomycin, 37° C. with 5% $CO_2$) to 90-100% confluence stage in 25 mL cell cultured flask. Cells were 'starved' in serum free medium (DMEM) for 16 hours. 10 nM bradykinin (in DMSO) solution was prepared in DMEM medium with 10% serum. 7 mL of 10 nM BK solution was added to the 25 mL cultured flask and incubated at 37° C. for 10 min. For the controls, the same amount of DMSO was added in DMEM medium with 10% serum. 7 mL of this medium with DMSO (<0.01%) was added to the 25 mL cultured flask and incubated at 37° C. for 10 min. After washing four times with cold (4° C.) 1×PBS, flasks were kept in dry ice/ethanol mixture for 15 min. Flasks were removed from dry ice/ethanol mixture and then 100 µL of lysis buffer (10 mM Tris, pH 7.4, 150 mM NaCl, 1 mM EDTA, 1 mM EGTA, 0.5% NP-40, 1% Triton X-100, 1% protease inhibitor cocktail, 1% ser/thr/tyrosine phosphatase inhibitor cocktails) was added into each flask. Flasks were kept on an end to end shaker in a cold room (4° C.) for 30 min and cells were collected from each flask with a cell scraper. Cells were sonicated and then centrifuged at 14000 rpm for 15 min, and the supernatant was used for Western blotting after total protein assay.

Example 8: Treatment of Fibroblast Cells with Different Protein Kinase C Activators Bradykinin or different specific protein kinase C activators are used to treat fibroblasts. Banked AC and AD skin fibroblasts are cultured to 80-100% confluence before they are "starved" in serum-free DMEM overnight. Cells are treated with 10 nM protein kinase C activator at 37 C. for different lengths of time to establish a time course for the protein kinase C activator-induced effects. The time point at which reactions are terminated immediately after application of protein kinase C activator is defined as "0 min" post-protein kinase C activator treatment. A control flask of cells for each cell line at each treatment time point is added with the identical volume of PBS. The reaction is terminated by removing the culture medium, rapidly rinsing the cells with precooled PBS, pH 7.4, and transferring the flask onto dry ice/ethanol. For cells obtained and cultured from fresh biopsy tissues, a concentration of 0.1 nM protein kinase C activator may be used. The treatment time is about 10 min at 37 C.

To prepare cell lysates from the treated cells, flasks are moved from dry ice/ethanol onto water ice. To each flask is added 1 ml of lysis buffer containing 10 mM Tris, pH 7.4, 150 mM NaCl, 1 mM EDTA, 1 mM EGTA, pH 8, 0.5% NP-40, 1% Triton X-100, 1% protease inhibitor cocktail (Sigma), 1% Ser/Thr, and tyrosine phosphatase inhibitor cocktails (Sigma). After rocking on an end-to-end shaker in a cold room for 30 min, cells are collected from each flask with a cell scraper. Cells are sonicated and centrifuged at 5000 rpm for 5 min, and the supernatant used for Western blotting.

Example 9: Western Blotting

Protocol 1: Cell lysates are treated with an equal volume of 2×SDS-sample buffer and boiled for 10 min. Proteins from each sample are resolved on a 4-20% mini-gradient gel and transferred onto a nitrocellulose membrane. Phosphorylated Erk1/2 is detected with an anti-phospho-Erk1/2 antibody using the SuperSignal ECL detection kit. In order to normalize the amount of phosphorylated Erk1/2 against the total amount of Erk1/2, after being blotted with an anti-phospho-Erk1/2 antibody, the same membrane is stripped with a stripping buffer containing 62.5 mM Tris-HCl, pH 6.7, 2% SDS, and 100 mM 2-mercaptoethanol at 60 C. for 45 min and then blotted with an anti-regular Erk1/2 antibody. Alternatively, duplicate samples resolved on SDS-PAGE and transferred to a nitrocellulose membrane are respectively blotted with anti-phospho- and anti-regular Erk antibodies. After being washed with 10 mM PBS, pH 7.4, containing 0.01% Tween 20 (three times for 10 min), the membrane is blotted with an anti-regular Erk1/2 antibody, from which the total amount of Erk1/2 loaded on the SDS gel is measured.

Protocol 2: Equal volumes of 2×SDS sample buffer were added to each cell lysate, and boiled for 10 minutes in boiling water bath. Electrophoresis was conducted on an 8-16% mini-gradient gel and transferred onto a nitrocellulose membrane. Total Erk1, Erk2 and the phosphorylated forms of Erk1 and Erk2 (p-Erk1, p-Erk2) were determined using specific antibodies.

Example 10: Data Analysis

Signals for both phosphorylated and regular forms of Erk1/2 are scanned with a Fujifilm LAS-1000 Plus scanner. The mean optical density of each protein band is measured using NIH Image software. Values from the phospho-Erk1/2 signals are normalized respectively against those of the total Erk1/2 signals. After normalization, data from each treated cell line is converted to a percentage of the basal control and subjected to statistical analyses.

Example 11: Immunocytochemistry

Fibroblast cells are grown on the surface of 2.5-cm-diameter glass coverslips coated with 0.02 mg polylysine. Upon treatment with bradykinin or another protein kinase C activator as described above, cells are rapidly rinsed with cold PBS, pH 7.4, and fixed with 4% formaldehyde in PBS, pH 7.4, at room temperature for 15 min. After being washed with PBS, pH 7.4, three times, each lasting 5 min, cells are penetrated with 0.1% Triton x-100 in PBS, pH 7.4, at room temperature for 30 min. After incubation with 10% normal horse serum in PBS, pH 7.4, at room temperature for 30 min, cells are incubated with anti-phospho-Erk1/2 antibody (1:200) at 4° C. overnight. Cells on the coverslips are washed with PBS, pH 7.4, three times and then an anti-mouse IgG labeled with fluorescein (Vector Laboratories) is added (1:200) and incubated with the cells at room temperature for 60 min. Following three washes with PBS, and sealing with Vectashield (Vector Laboratories), immunostaining signals in the cells are observed with a Nikon fluorescene microscope. The intensity of the immunocytochemistry signals in the cell images is measured with Bio-Rad Quantity One software (BioRad) and Tnimage. For localization of the BK or protein kinase C activator receptors in the skin fibroblasts, a monoclonal anti-BK B2 antibody, or anti protein kinase C activator antibody is applied to the normal fibroblasts, followed by incubation with Cy5-conjugated anti-mouse IgG. The resulting immunoreactive signals are imaged with a fluorescence microscope.

The invention claimed is:

1. A method for determining the absence of Alzheimer's Disease in a subject comprising:
   a) determining the result of an Alzheimer's disease-specific molecular biomarker (ADSMB);
   b) contacting cells from the subject with an amyloid beta peptide;
   c) determining the result of an ADSMB after said contact with the amyloid beta peptide, and
   d) evaluating whether the contact in step b) induces an Alzheimer's disease phenotype in the cells based on the determinations in steps a) and c),
   wherein the result of the ADSMB is determined by:
      i) contacting cells from said subject with an agent that is a protein kinase C activator;
      ii) measuring the ratio of phosphorylated extracellular signal-regulated kinase 1 (pErk1) to phosphorylated extracellular signal-regulated kinase 2 (pErk2) in the cells after contact with the agent in step i);
      iii) measuring the ratio of pErk1 to pErk2 in cells from said subject that have not been contacted with the agent of step i); and
      iv) determining the result of the ADSMB by subtracting the ratio obtained in step iii) from the ratio obtained in step ii),
   and wherein the contact in step b) induces an Alzheimer's disease phenotype in the cells if the result of the ADSMB from step a) is a negative value or zero and the result of the ADSMB from step c) is a positive value greater than zero, and wherein the absence of Alzheimer's disease in the subject is indicated if the contact in step b) induces the Alzheimer's disease phenotype in the cells.

2. The method of claim 1, wherein the presence of Alzheimer's Disease in said subject is indicated if there is no significant alteration or change from the value of the ADSMB from step a) to the value of the ADSMB from step c).

3. The method of claim 1, wherein said amyloid beta peptide is Aβ (1-42).

4. The method of claim 1, wherein said protein kinase C activator is selected from the group consisting of bradykinin, bryostatin, bombesin, cholecystokinin, thrombin, prostaglandin F2α and vasopressin.

5. The method of claim 1, wherein said cells are peripheral cells.

6. The method of claim 5, wherein said cells are selected from the group consisting of fibroblasts, skin cells, and buccal mucosa cells from saliva, blood, urine or cerebrospinal fluid.

7. The method of claim 1, wherein said method comprises an in vitro assay.

* * * * *